(12) United States Patent
Challoner et al.

(10) Patent No.: US 8,664,187 B2
(45) Date of Patent: Mar. 4, 2014

(54) METHODS OF TREATMENT OF ENDOBRONCHIAL INFECTIONS

(75) Inventors: Peter Challoner, Emeryville, CA (US); Carlos Rodriguez, Emeryville, CA (US); Emil Samara, Emeryville, CA (US); Thomas E Tarara, Burlingame, CA (US); John D Lord, San Carlos, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/404,359

(22) Filed: Feb. 24, 2012

(65) Prior Publication Data

US 2012/0148641 A1    Jun. 14, 2012

Related U.S. Application Data

(63) Continuation of application No. 12/984,110, filed on Jan. 4, 2011, now abandoned, which is a continuation of application No. 11/570,584, filed as application No. PCT/US2005/021952 on Jun. 20, 2005, now abandoned.

(60) Provisional application No. 60/580,848, filed on Jun. 18, 2004.

(51) Int. Cl.
*A61K 31/70* (2006.01)

(52) U.S. Cl.
USPC .......................................................... 514/35

(58) Field of Classification Search
USPC .......................................................... 514/35
See application file for complete search history.

(56) References Cited

U.S. PATENT DOCUMENTS

| | | |
|---|---|---|
| 3,906,950 A | 9/1975 | Cocozza |
| 4,013,075 A | 3/1977 | Cocozza |
| 4,069,819 A | 1/1978 | Valentini et al. |
| 4,667,668 A | 5/1987 | Wetterlin |
| 4,668,218 A | 5/1987 | Virtanen |
| 4,805,811 A | 2/1989 | Wetterlin |
| 4,995,385 A | 2/1991 | Valentini et al. |
| 5,388,572 A | 2/1995 | Mulhauser et al. |
| 5,458,135 A | 10/1995 | Patton et al. |
| 5,508,269 A | 4/1996 | Smith |
| 5,522,385 A | 6/1996 | Lloyd et al. |
| 5,740,794 A | 4/1998 | Smith et al. |
| 5,775,320 A | 7/1998 | Patton et al. |
| 5,785,049 A | 7/1998 | Smith et al. |
| 5,826,633 A | 10/1998 | Parks et al. |
| 6,089,228 A | 7/2000 | Smith et al. |
| 6,387,886 B1 | 5/2002 | Montgomery |
| 6,890,907 B2 | 5/2005 | Speirs et al. |
| 6,946,339 B2 | 9/2005 | Herzum |
| 2003/0129140 A1 | 7/2003 | Tarara |
| 2003/0143162 A1 | 7/2003 | Speirs et al. |

FOREIGN PATENT DOCUMENTS

| | | |
|---|---|---|
| CA | 2421974 A1 | 9/2001 |
| CN | 1493297 | 5/2004 |
| CN | 1493297 A | 5/2004 |
| EP | 0129985 A1 | 1/1985 |
| EP | 0467172 A1 | 1/1992 |
| EP | 0472598 A1 | 3/1992 |
| WO | 9013328 A1 | 11/1990 |
| WO | 9509616 A1 | 4/1995 |
| WO | 9531479 A1 | 11/1995 |
| WO | 9632096 A1 | 10/1996 |
| WO | 0035461 A1 | 6/2000 |
| WO | WO 00/35461 | 6/2000 |
| WO | 0113891 A2 | 3/2001 |
| WO | 0113893 A2 | 3/2001 |
| WO | 0185137 A2 | 11/2001 |
| WO | WO 01/85136 | 11/2001 |
| WO | 03005411 A2 | 1/2003 |
| WO | WO 03/005411 | 1/2003 |
| WO | 03041776 A1 | 5/2003 |
| WO | 03041777 A1 | 5/2003 |
| WO | 03053411 A1 | 7/2003 |
| WO | 03057593 A1 | 7/2003 |
| WO | WO 03/053411 | 7/2003 |
| WO | 03094890 A1 | 11/2003 |
| WO | WO 03/094890 | 11/2003 |

OTHER PUBLICATIONS

Geller, D.E. et al., "Pharmacokinetics and Bioavailability of Aerosolized Tobramycin in Cystic Fibrosis", Chest 122(1):219-226, Jul. 2002.
Newhouse, M.T. et al., "Inhalation of a Dry Powder Tobramycin PulmoSphere Formulation in Healthy Volunteers", Chest 124(1):360-366, Jul. 2003.
Ramsey, B.W. et al., "Intermittent Administration of Inhaled Tobramycin in Patients With Cystic Fibrosis", New England Journal of Medicine 340(1):23-30, Jan. 1999.
Office Action mailed Jul. 6, 2009, issued in corresponding Russian Federation Patent Application No. 2007101906, filed Jun. 20, 2005.
Office Action dated Aug. 4, 2009, issued in corresponding Israeli Patent Application No. 179873, filed Jun. 20, 2005.
Semykin, S.Y., "Effectiveness and Safety in the Use of Ciprofloxacin in Treating the Recurrent Bronchopulmonary Process in Children With Cystic Fibrosis", Dissertation Submitted for the Academic Degree of Candidate in Medical Sciences. Moscow, 2002, pp. 8-11, 22-23.
Abbott J et al "Treatment compliance in adults with cystic fibrosis" Thorax 49:115-120 (1994).
Ballmann Manfred et al "Long term follow-up of changes in FEV1 and treatment intensity during *Pseudomonas aeruginosa* colonisation in patients with cystic fibrosis" Thorax 53:732-737 (1998).
Brummett RE "Drug-induced Ototoxicity" Drugs 19:412-428 (1980).
Collins Francis S "Cystic Fibrosis: Molecular Biology and Therapeutic Implications" Science 256:774-779 (1992).
Conway SP et al "Compliance with treatment in adult patients with cystic fibrosis" Thorax 51:29-33 (1996).
Corey Mary et al "Longitudinal analysis of pulmonary function decline in patients with cystic fibrosis" J Pediatr 131:809-814 (1997).
Davis Pamela B et al "Cystic Fibrosis" Am J Respir Crit Care Med 154:1229-1256 (1996).

(Continued)

*Primary Examiner* — Elli Peselev
(74) *Attorney, Agent, or Firm* — Michael J. Mazza

(57) ABSTRACT

The present invention provides methods for the treatment of an endobronchial infection in a patient by administering to the endobronchial system of the patient a dry powder aerosol composition comprising from 90 to 130 mg of an aminoglycoside antibiotic one to three times a day for a first treatment period of 20 to 36 days.

17 Claims, 4 Drawing Sheets

(56) References Cited

OTHER PUBLICATIONS

Demko Catherine A et al "Gender Differences in Cystic Fibrosis: *Pseudomonas aeruginosa* Infection" J Clin Epidemiol 48(8):1041-1049 (1995).

Eisenberg Jay et al "A Comparison of Peak Sputum Tobramycin Concentration in Patients with Cystic Fibrosis Using Jet and Ultrasonic Nebulizer Systems" Chest 111:955-962 (1997).

Fitzsimmons Stacey C "The changing epidemiology of cystic fibrosis" J Pediatr 122:1-9 (1993).

Fuchs Henry J et al "Effect of Aerosolized Recombinant Human DNase on Exacerbations of Respiratory Symptoms and on Pulmonary Function in Patients with Cystic Fibrosis" N Engl J Med 331:637-642 (1994).

Geller David E et al "Pharmacokinetics and Bioavailability of Aerosolized Tobramycin in Cystic Fibrosis" Chest 122:219-226 (2002).

Henry Richard L et al "Mucoid *Pseudomonas aeruginosa* is a Marker of Poor Survival in Cystic Fibrosis" Pediatr Pulmonol 12:158-161 (1992).

"Guide for the Evaluation of Hearing Handicap" JAMA 241(19):2055-2059 (1979).

Kerem Eitan et al "Prediction of Mortality in Patients with Cystic Fibrosis" N Engl J Med 326:1187-1191 (1992).

Koch Christian et al "Pathogenesis of cystic fibrosis" Lancet 341:1065-1069 (1993).

Konig Peter et al "Short-Term and Long-Term Effects of Albuterol Aerosol Therapy in Cystic Fibrosis: A Preliminary Report" Pediatr Pulmonol 20:205-214 (1995).

Konstan Michael W et al "Effect of High-Dose Ibuprofen in Patients with Cystic Fibrosis" N Engl J Med 332:848-854 (1995).

Levy Jack et al "Bioactivity of Gentamicin in Purulent Sputum from Patients with Cystic Fibrosis or Bronchiectasis: Comparison with Activity in Serum" J Infect Dis 148(6):1069-1076 (1983).

MacLusky Ian B et al "Long-Term Effects of Inhaled Tobramycin in Patients with Cystic Fibrosis Colonized with *Pseudomonas aeruginosa*" Pediatr Pulmonol 7:42-48 (1989).

Neu Harold C "Tobramycin: an Overview" J Infect Dis 134:S3-S19 (1976).

Newhouse Michael T "Inhalation of a Dry Powder Tobramycin PulmoSphere Formulation in Healthy Volunteers" Chest 124:360-366 (2003).

Pamukcu A et al "Effects of *Pseudomonas aeruginosa* Colonization on Lung Function and Anthropometric Variables in Children with Cystic Fibrosis" Pediatr Pulmonol 19:10-15 (1995).

"Physical Tests and Determinations. Aerosols, Metered-Dose Inhalers, and Dry Powder Inhalers" Pharmacopeia US 26th Rev, Natl Formulary 21st Ed, Ch 601 (2003).

Ramsey Bonnie W et al "Response to Letter to the Editor: Aerosolised Tobramycin in Patients with Cystic Fibrosis" N Eng J Med 329:1660 (1993).

Ramsey Bonnie W et al "Intermittent Administration of Inhaled Tobramycin in Patients with Cystic Fibrosis" N Engl J Med 340:23-30 (1999).

Reisman John J et al "Role of conventional physiotherapy in cystic fibrosis" J Pediatr 113:632-636 (1988).

Rosenfeld Margaret at al "Aerosolized Antibiotics for Bacterial Lower Airway Infections: Principles, Efficacy, and Pitfalls" Clin Pulm Med 4(2):101-112 (1997).

Semykim Sergei Yurevich "Effectiveness and Safety in the Use of Ciprofloxacin in Treating the Recurrent Bronchopulmonary Process in Children with Cystic Fibrosis" abstract candidate dissertation, Moscow pp. 8-11, 22-23 (2002).

Touw DJ et al "Inhalation of antibiotics in cystic fibrosis" Eur Respir J 8:1594-1604 (1995).

Winnie Glenna B et al "Respiratory Tract Colonization with *Pseudomonas aeruginosa* in Cystic Fibrosis: Correlations Between Anti-*Pseudomonas aeruginosa* Antibody Levels and Pulmonary Function" Pediatr Pulmonol 10:92-100 (1991).

Konstan Michael W et al "Infection and Inflammation of the Lung in Cystic Fibrosis" Cystic Fibrosis, Davis ed, Dekker NY pub, Ch 8, pp. 219-276 (1993).

Cystic Fibrosis Foundation Patient Registry Annual Data Report 2004.

International Search Report, PCT/US05/21952 (Sep. 23, 2005).

Supplementary EP Search Report, EP 05766064 (Apr. 1, 2009).

METHODS OF TREATMENT OF ENDOBRONCHIAL INFECTIONS

This application is a continuation of U.S. application Ser. No. 12/984,110 filed Jan. 4, 2011, which is a continuation of U.S. application Ser. No. 11/570,584, filed Sep. 4, 2007 (abandoned), which is a 35 U.S.C. 371 national stage entry of international application No. PCT/US05/21952, filed Jun. 20, 2005, which claims priority to U.S. Provisional Application No. 60/580,848, filed Jun. 18, 2004, the contents of each of which are hereby incorporated in their entirety.

This application claims the benefit of U.S. Provisional Application No. 60/580,848, filed Jun. 18, 2004, which is incorporated herein by reference in its entirety.

FIELD OF THE INVENTION

The present invention relates to new and improved methods for treatment of susceptible endobronchial infections in patients with dry powder formulations of aminoglycoside antibiotics, such as tobramycin.

BACKGROUND OF THE INVENTION

Cystic fibrosis (CF) is the most common life-shortening genetic disease in the United States and Northern Europe, affecting approximately 30,000 individuals in the United States (Cunningham, J. C. et al., "An Introduction to Cystic Fibrosis for Patients and Families," 5th ed., Bethesda: Cystic Fibrosis Foundation (2003)) and a similar number of individuals in Western Europe. The genetic defect in this autosomal recessive disease is a mutation in the CF transmembrane conductance regulator (CFTR) gene, which codes for a chloride-channel protein (Collins, F. S., "Cystic Fibrosis Molecular Biology and Therapeutic Implications," Science 256:774-779 (1992)). Persons with CF typically suffer from chronic endobronchial infections, sinusitis, and malabsorption due to pancreatic insufficiency, increased salt loss in sweat, obstructive hepatobiliary disease, and reduced fertility (FitzSimmons, S. C., "The Changing Epidemiology of Cystic Fibrosis," J Pediatr 122:1-9 (1993)). Respiratory disease is a major cause of morbidity and accounts for 90% of mortality in persons with CF (Cystic Fibrosis Foundation, Cystic Fibrosis Foundation Patient Registry 2003 Annual Data Report, Bethesda, Md.: Cystic Fibrosis Foundation, (2004); Davis, P. B. et al., "Cystic fibrosis," Amer J. Respir Crit Care Med 154 (5):1229-56 (1996)). Lung function (measured as forced expiratory volume at 1 second ($FEV_1$% predicted) is a significant predictor of survival in CF. Two-year survival for a given population of persons with CF is reduced 2-fold with each 10% reduction in $FEV_1$% predicted, and persons with $FEV_1$ below 30% of predicted have a 2-year survival below 50% (Kerem, E. et al., "Prediction of Mortality in Patients with Cystic Fibrosis," N Engl J Med 326:1187-1191 (1992)). Rates of lung function loss vary both between individuals and over time for a given individual. Retrospective longitudinal analyses show rates of decline ranging from less than 2% of $FEV_1$% predicted per year to greater than 9% $FEV_1$% predicted per year, with overall rate of decline strongly associated with age of death (Corey, M. et al., "Longitudinal Analysis of Pulmonary Function Decline in Patients with Cystic Fibrosis," J Pediatr 131 (6):809-1 (1997)).

CF patients suffer from thickened mucus caused by perturbed epithelial ion transport that impairs lung host defenses, resulting in increased susceptibility to early endobronchial infections with Staphylococcus aureus, Haemophilus influenzae, and P. aeruginosa. By adolescence, a majority of persons with CF have P. aeruginosa present in their sputum (Cystic Fibrosis Foundation Patient Registry 2003 Annual Data Report (2004)). Chronic endobronchial infections, particularly with P. aeruginosa, provoke a persistent inflammatory response in the airway that accelerates progressive obstructive disease characterized by diffuse bronchiectasis (Davis, P. B. et al. (1996), supra; Winnie, G. B. et al., "Respiratory Tract Colonization with Pseudomonas aeruginosa in Cystic Fibrosis: Correlations Between Anti-Pseudomonas aeruginosa Antibody Levels And Pulmonary Function," Pediatr Pulmonol 10:92-100 (1991); Ballman, M. et al. "Long Term Follow Up of Changes in $FEV_1$ and Treatment Intensity During Pseudomonas Aeruginosa Colonisation in Patients with Cystic Fibrosis," Thorax 53:732-737 (1998); Pamukcu, A. et al., "Effects of Pseudomonas aeruginosa Colonization on Lung Function and Anthropometric Variables in Children with Cystic Fibrosis," Pediatr Pulmonol 19:10-15 (1995)). A link between acquisition of chronic endobronchial P. aeruginosa infection, lung inflammation, loss of lung function, and ultimate death is suggested by significantly decreased survival associated with chronic P. aeruginosa infection (Henry, R. L. et al., "Mucoid Pseudomonas aeruginosa is a Marker of Poor Survival in Cystic Fibrosis," Pediatr Pulmonol 12 (3):158-61 (1992)), and by the significant association of early acquisition of chronic P. aeruginosa infection and childhood mortality (Demko, C. A. et al., "Gender Differences in Cystic Fibrosis: Pseudomonas aeruginosa Infection," J Clin Epidemiol 48:1041-1049 (1995)). Chronic Therapies that either suppress bacterial loads in the lung (MacLusky, I. B. et al, "Long-term Effects of Inhaled Tobramycin in Patients with Cystic Fibrosis Colonized with Pseudomonas aeruginosa," Pediatr Pulmonol 7 (1):42-8 (1989)) or suppress resulting inflammation (Konstan, M. W. et "Effect of high-dose Ibuprofen in Patients with Cystic Fibrosis," N Engl J Med 332 (13):848-54 (1995)) have been shown to reduce rates of lung function decline in infected patients.

Historically, the standard therapy for P. aeruginosa endobronchial infections was 14 to 21 days of parenteral antipseudomonal antibiotics, typically including an aminoglycoside. However, parenteral aminoglycosides, as highly polar agents, penetrate poorly into the endobronchial space. To obtain adequate drug concentrations at the site of infection with parenteral administration, serum levels approaching those associated with nephro-, vestibule-, and oto-toxicity are required ("American Academy of Otolaryngology. Guide for the evaluation of hearing handicap," JAMA 241 (19):2055-9 (1979); Brummett, R. E., "Drug-induced ototoxicity," Drugs 19:412-28 (1980)).

Inhalation administration of aminoglycosides offers an attractive alternative, delivering high concentrations of antibiotic directly to the site of infection in the endobronchial space while minimizing systemic bioavailability (Touw, D. J. et al., "Inhalation of Antibiotics in Cystic Fibrosis," Eur Respir J 8:1594-604 (1995); Rosenfeld, M. et al., "Aerosolized Antibiotics for Bacterial Lower Airway Infections: Principles, Efficacy, and Pitfalls," Clinical Pulmonary Medicine 4 (2):101-12 (1997)).

The current standard of treatment of P. aeruginosa infections in CF patients is TOBI® tobramycin solution for inhalation, a preservative-free, stable, and convenient formulation of tobramycin (60 mg/mL tobramycin in 5 mL of ¼ normal saline) for administration via jet nebulizer, developed by PathoGenesis Corporation, Seattle, Wash. (now Chiron Corporation, Emeryville, Calif.). The combination of a 5 mL BID TOBI dose (300 mg tobramycin) and the PARI LC PLUS/PulmoAide compressor delivery system was approved by the FDA under NDA 50-753, December 1997, as a chronic intermittent therapy for the management of *P. aeruginosa* in CF patients, and remains the industry standard for this purpose. The process of inhalation of the commercially available 300 mg TOBI dose can take 20 minutes per dose with additional time required for set-up and nebulizer cleaning. The aerosol administration of a 5 ml dose of a formulation containing 300 mg of tobramycin in quarter normal saline for the suppression of *P. aeruginosa* in the endobronchial space of a patient is also disclosed in U.S. Pat. No. 5,508,269, the disclosure of which is incorporated herein in its entirety by this reference.

Tobramycin is an aminoglycoside antibiotic produced by the actinomycete, *Streptomyces tenebrarius*. Low concentrations of tobramycin (<4 µg/mL) are effective in inhibiting the growth of many Gram-negative bacteria and under certain conditions may be bactericidal (Neu, H. C., "Tobramycin: an overview," *J Infect Dis* 134: Suppl: S3-19 (1976)). Tobramycin is poorly absorbed across mucosal surfaces, conventionally necessitating parenteral administration. In addition, tobramycin activity is inhibited by purulent sputum: high concentrations of divalent cations, acidic conditions, increased ionic strength and macromolecules that bind the drug all inhibit tobramycin in this environment. It is estimated that 5 to 10 times higher concentrations of tobramycin are required in the sputum to overcome these inhibitory effects (Levy, J. et al., "Bioactivity of Gentamicin in Purulent Sputum from Patients with Cystic Fibrosis or Bronchiectasis: Comparison with Activity in Serum," *J Infect Dis* 148 (6): 1069-76 (1983)).

The effectiveness of delivery of the poorly absorbed antibiotic tobramycin to the airway by the aerosol route of cystic fibrosis (CF) patients has been well documented. Much of this work has been done toward treatment of chronic lung infections with *P. aeruginosa* in cystic fibrosis (CF) patients. For example, a multicenter, double blind, placebo-controlled, crossover trial of 600 mg tid of aerosolized tobramycin for endobronchial infections due to *P. aeruginosa* in 71 CF patients demonstrated a significant reduction in sputum density of this pathogen as well as improved spirometry in the treatment group. Emergence of *P. aeruginosa* strains highly resistant to tobramycin (defined as MIC ≥128 µg/mL) was comparable in the placebo and treatment groups. The presence in the sputum of Gram-negative organisms other than *P. aeruginosa* intrinsically resistant to tobramycin occurred with equal frequency during administration of tobramycin or placebo (Ramsey, B. et al., "Response to Letter to the Editor: Aerosolized Tobramycin in Patients with Cystic Fibrosis," *N Engl J Med* 329:1660 (1993)).

Although this regimen was found to be both safe and efficacious, it is costly and inconvenient. A survey of the MICs for *P. aeruginosa* isolates from initial sputum cultures for patients at the Children's Hospital CF Center, Seattle, Wash., in 1993 found that 90% of isolates had MICs ≤16 µg/mL and 98% of all isolates had MICs ≤128 µg/mL. This survey suggested that achieving a sputum tobramycin concentration of 128 µg/mL should effectively treat endobronchial infections in CF patients (Levy, J. et al., "Bioactivity of Gentamicin in Purulent Sputum from Patients with Cystic Fibrosis or Bronchiectasis: Comparison with Activity in Serum," *J Infect Dis* 148 (6):1069-76 (1983)).

A randomized, crossover study compared the ability of several nebulizers to deliver tobramycin by measuring peak sputum tobramycin concentrations in samples collected ten minutes after completion of the aerosol dose. This study administered TOBI® tobramycin solution for inhalation, PathoGenesis Corporation, Seattle, Wash. (now Chiron Corporation, Emeryville, Calif.), containing 60 mg/mL tobramycin in 5 mL one quarter (¼) normal saline, using the PARI® LC jet nebulizer, PARI Respiratory Equipment, Inc., Richmond, Va. This delivery system was shown to deliver a mean peak sputum tobramycin concentration of 678.8 µg/g (s.d. 661.0 µg/g), and a median peak sputum concentration of 433.0 µg/g. Only 13% of patients had sputum levels ≤128 µg/g; 87% of patients achieved sputum levels of ≥128 µg/g (Eisenberg, J. et al., "A Comparison of Peak Sputum Tobramycin Concentration in Patients With Cystic Fibrosis Using Jet and Ultrasonic Nebulizer Systems. Aerosolized Tobramycin Study Group," *Chest* 111 (4):955-962 (1997)). Recently, the PARI® LC jet nebulizer has been modified with the addition of one-way flow valves, and renamed the PARI® LC PLUS. The one-way valves in the PARI® LC PLUS have been described as permitting the delivery of more drug than the PARI® LC jet nebulizer, while decreasing the potential for accidental spillage and allowing for the use of an expiratory filter. Experience has shown that mean peak sputum tobramycin concentrations achieved using the PARI LC PLUS jet nebulizer are significantly higher than those, using the PARI® LC jet nebulizer as described in Eisenberg et al. (1997), supra.

In addition to the foregoing, two placebo-controlled, multicenter, randomized, double blind clinical trials of intermittent administration of inhaled liquid aerosol tobramycin in cystic fibrosis patients with *P. aeruginosa* infection were reported in Ramsey, B. W. et al., "Intermittent Administration of Inhaled Tobramycin in Patients with Cystic Fibrosis. Cystic Fibrosis Inhaled Tobramycin Study Group." *N. Engl. J. Med* 340 (1):23-30 (1999). In these studies, five hundred twenty subjects were randomized to receive either 300 mg inhaled tobramycin or placebo twice daily for 28 days followed by 28 days off study drug. Subjects continued on treatment or placebo for three "on-off" cycles for a total of 24 weeks. Efficacy variables included sputum *P. aeruginosa* density. Tobramycin-treated patients had an average 0.8 $\log_{10}$ decrease in *P. aeruginosa* density from Week 0 to Week 20, compared with a 0.3 $\log_{10}$ increase in placebo-treated patients (P<0.001). Tobramycin-treated patients had an average 1.9 $\log_{10}$ decrease in *P. aeruginosa* density from Week 0 to Week 4, compared with no change in placebo-treated patients (P<0.001).

U.S. Pat. No. 6,890,907 and United States Published Patent Application 2003/0143162 A1 disclose that patients suffering from an endobronchial infection can be effectively treated by administering to the patient for inhalation a dose of 4.0 ml, or less, of a nebulized liquid aerosol formulation comprising from about 60 to about 200 mg/ml of an aminoglycoside antibiotic, such as tobramycin, in a physiologically acceptable carrier, in a time period of less than about 10 minutes. The more efficient administration of the aminoglycoside formulation permits substantially smaller volumes of liquid aminoglycoside than the conventional administration regime to be administered in substantially shorter periods of time, thereby reducing the costs of administration and drug waste. Moreover, the formulations were shown to contain a minimal yet efficacious amount of aminoglycoside formulated in a relatively small volume of a physiologically acceptable solution, thereby reducing irritation of the lungs after inhalation of the aminoglycoside formulation.

In addition to inhaled antibiotics such as the commercially available TOBI® product, a variety of other chronic therapies are routinely prescribed to reduce the destructive cycles of obstruction, infection, and inflammation in the CF lung. Aggressive Airway Clearance Therapy (Reisman, J. J. et al., "Role of conventional physiotherapy in cystic fibrosis," *J Pediatr* 113 (4):632-6 (1988)), inhaled bronchodilators (Konig P et al., "Short-term and Long-term Effects of Albuterol Aerosol Therapy in Cystic Fibrosis: A Preliminary Report," *Pediatr Pulmonol* 20 (4):205-14 (1995)), and mucolytics such as recombinant human dornase alpha (rhDNase; Fuchs, H. J. et al., "Effect of Aerosolized Recombinant Human DNase on Exacerbations of Respiratory Symptoms and on Pulmonary Function in Patients with Cystic Fibrosis. The Pulmozyme Study Group," *N Engl J Med* 331 (10):637-42 (1994)) are all prescribed chronically, creating a potential for significant treatment burden for persons with CF. It has been shown that adherence to therapies is a significant problem for persons with CF (Conway, S. P. et al., "Compliance with treatment in adult patients with cystic fibrosis," *Thorax* 51 (1):29-33 (1996)) and that lack of compliance can vary by specific treatment (Abbott J et al., "Treatment Compliance in Adults with Cystic Fibrosis," *Thorax* 49 (2):115-20 (1994)).

As described above, the commercially available TOBI® liquid aerosol tobramycin solution for inhalation has proven to be highly effective in treating *P. aeruginosa* infections in CF patients. Given the treatment burden and adherence challenges associated with preservation of lung function in persons with CF, improvements in existing therapies that reduce treatment administration time or increase convenience of treatment for patients will facilitate patient adherence and resulting therapeutic efficacy. Accordingly, there is a need for new and improved methods and devices for the delivery of aminoglycoside antibiotic compounds to a patient by inhalation to reduce administration costs, increase patient compliance and enhance overall effectiveness of the inhalation therapy.

SUMMARY OF THE INVENTION

The present invention provides methods for the treatment of endobronchial infections in a patient, comprising administering to the endobronchial system of the patient a dry powder aerosol composition comprising from 90 to 130 mg of an aminoglycoside antibiotic one to three times a day for a first treatment period of 20 to 36 days. In the practice of the invention, the first treatment period may be followed by a second non-treatment period wherein no aminoglycoside antibiotic is administered to the endobronchial system of the patient. For the treatment of virulent infections, the cycle of the first treatment period of aminoglycoside treatment followed by the second non-treatment period wherein no aminoglycoside antibiotic is administered to the endobronchial system of the patient may be repeated two or more times until the desired antibacterial effect is obtained. In the case of chronic infections, such as infections occurring in cystic fibrosis patients, the first and second treatment periods may be repeated a multiplicity of times throughout the medical treatment of the patient.

The methods of the invention are useful for treating any endobronchial infection that is susceptible to an aminoglycoside antibiotic, such as a pseudomonal endobronchial infection associated with cystic fibrosis.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
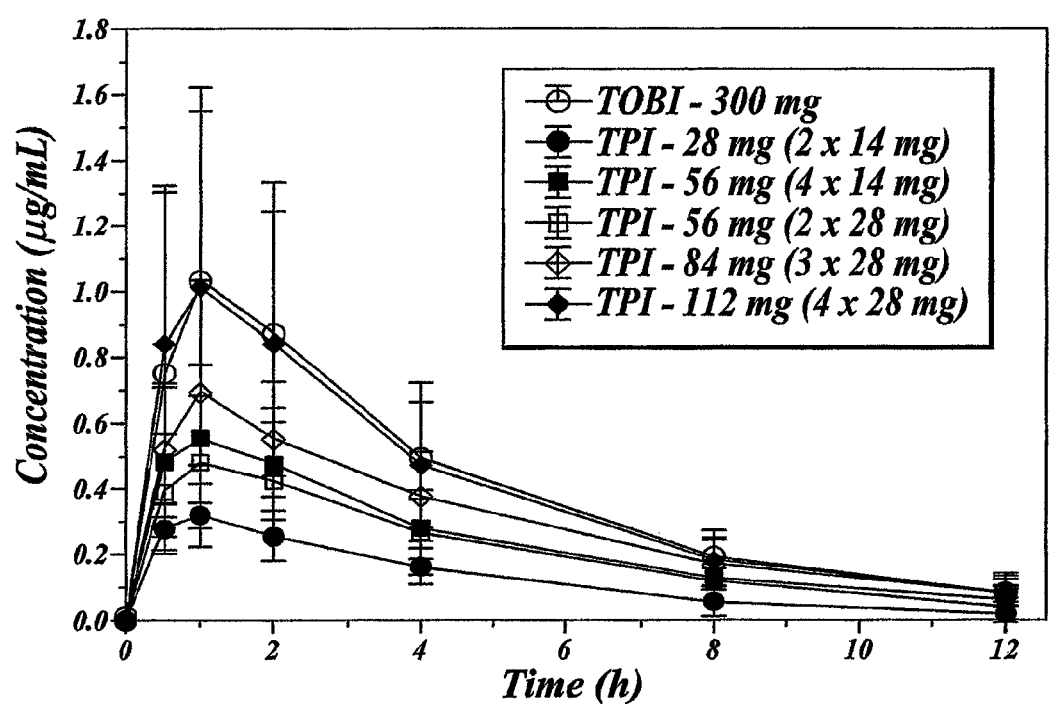
FIG. 1 shows mean serum concentration of tobramycin in subjects at various times after administration of a defined dosage of TPI and TOBI.

Unless specifically defined herein, all terms used herein have the same meaning as they would to one skilled in the art of the present invention. The following abbreviations are used herein:

| Abbreviation | Meaning |
| --- | --- |
| AE | adverse event |
| ALT | alanine aminotransferase |
| AUC | area under curve |
| BID | twice daily |
| BUN | blood urea nitrogen |
| $CaCl_2$ | calcium chloride |
| CF | cystic fibrosis |
| CFC | chlorofluorocarbon |
| $C_{max}$ | maximum concentration |
| CFTR | cystic fibrosis transmembrane conductance regulator |
| DPI | dry powder inhaler |
| DSPC | 1,2 distearoyl-sn-glycero-3-phosphocholine |
| FDA | United States Food and Drug Administration |
| $FEV_1$ | forced expiratory volume at 1 second |
| FVC | forced vital capacity |
| $FEF_{25-75}$ | forced expiratory flow between 25% and 75% |
| HPMC | 2-hydroxyproplymethylcellulose |
| IRB | Institutional Review Board |
| IVRS | Interactive Voice Response System |
| MedDRA | Medical Dictionary for Regulatory Activities |
| MIC | minimal inhibitory concentration |
| *P. aeruginosa* | *Pseudomonas aeruginosa* |
| PFOB | perfluorooctyl bromide |
| QPIT | quantitative pilocarpine iontophoresis test |
| SAE | serious adverse event |
| $t_{max}$ | time to maximum concentration |
| TOBI® | 300 mg Tobramycin Solution for Inhalation, Chiron Corporation, Emeryville, CA |
| TIP | Tobramycin Inhalation Powder |

In one aspect the present invention provides methods for the treatment of endobronchial infections in a patient, comprising administering to the endobronchial system of the patient a dry powder aerosol composition comprising from 90 to 130 mg of an aminoglycoside antibiotic one to three times a day for a first treatment period of 20 to 36 days. In the practice of the invention, the first treatment period may be followed by a second non-treatment period wherein no aminoglycoside antibiotic is administered to the endobronchial system of the patient. For the treatment of virulent infections, the cycle of the first treatment period of aminoglycoside treatment followed by the second non-treatment period wherein no aminoglycoside antibiotic is administered to the endobronchial system of the patient may be repeated two or more times until the desired antibacterial effect is obtained. In the case of chronic infections, such as infections occurring in cystic fibrosis patients, the first and second treatment periods may be repeated a multiplicity of times throughout the medical treatment of the patient.

In another aspect, the present invention provides the use of an aminoglycoside antibiotic in the preparation of a medicament for the treatment of endobronchial infections in a patient by administering to the endobronchial system of the patient in a first treatment period a dry powder aerosol composition comprising from 90 to 130 mg of an aminoglycoside antibiotic one to three times a day for a first treatment period of 20 to 36 days. In the practice of this aspect of the invention, the first treatment period may similarly be followed by a second non-treatment period wherein no aminoglycoside antibiotic is administered to the endobronchial system of the patient, and the first and second treatment periods may be repeated, substantially as described herein.

The methods of this aspect of the invention each include the step of administering, by inhalation, to a human or animal subject, in need of such administration, a therapeutically effective amount of an aerosol powder comprising 20% by weight to 90% by weight of an aminoglycoside antibiotic and a physiologically acceptable carrier, wherein the powder comprises particles, and wherein at least 50% of the particles have an aerodynamic diameter in the range of from 1 μm to 5 μm.

The term "endobronchial infection" refers to a bacterial infection located within a bronchus of the lungs. Examples of endobronchial infections that can be treated using the methods of the present invention include infections by gram negative organisms, such as *Pseudomonas aeruginosa, Staphylococcus aureus, Haemophilus influenzae, Burkholderia cepacia, Stenotrophomonas maltophilia*, and *Alcaligenes xiloxidants*. The methods of this aspect of the present invention can be used, for example, to treat human beings suffering from an endobronchial infection associated with cystic fibrosis, such as, e.g., a *Pseudomonas aeruginosa* infection.

Aminoglycoside antibiotics useful in the practice of the invention, include, for example, gentamicin, amikacin, kanamycin, streptomycin, neomycin, netilmicin, paramecin and tobramycin. A presently preferred aminoglycoside antibiotic for use in the practice of the present invention is tobramycin. The aminoglycoside antibiotic is typically administered in the form of a pharmaceutically acceptable salt (e.g., sulfate, citrate, ascorbate, gluconate, carbonate, tartarate, succinate, acetate, or phosphate) or ester.

In the practice of the present invention, the aerosol powder is inhaled by the human or animal subject, and thereby enters the lungs of the human or animal subject. The aerosol powder comprises particles that comprise the aminoglycoside antibiotic. It has been found that aerosol powders (comprising an aminoglycoside antibiotic) wherein at least 50% of the particles have an aerodynamic diameter in the range of from 1 μm to 5 μm effectively penetrate into the lungs of the human or animal subject, thereby effectively delivering the aminoglycoside antibiotic to the lungs of the subject. By way of example, some aerosol powders (comprising an aminoglycoside antibiotic) useful in the practice of the present invention comprise particles wherein at least 60% of the particles, or at least 70% of the particles, or at least 80% of the particles, or at least 90% of the particles, or at least 95% of the particles, have an aerodynamic diameter in the range of from 1 μm to 5 μm.

The term "aerodynamic diameter" refers to the diameter of a unit-density sphere having the same terminal settling velocity as the particle in question (see, e.g., "Aerosol Measurement: Principles, Techniques and Applications". Edited by Klaus Willeke and Paul A. Baron. Van Nostrand Reinhold, New York, 1993). Aerodynamic diameter is used, for example, to predict where such particles will be deposited in the respiratory tract.

"Mass median aerodynamic diameter" (abbreviated as MMAD) is a measure of the aerodynamic size of a dispersed particle. The aerodynamic size distribution defines the manner in which an aerosol deposits during inhalation, and is the diameter of a unit density sphere having the same settling velocity, generally in air, as the particle. The aerodynamic diameter encompasses particle shape, density and physical size of a particle. When there is a log-normal distribution, the aerodynamic size distribution may be characterized by the mass median aerodynamic diameter (MMAD). As used herein, MMAD refers to the midpoint or median of the aerodynamic particle size distribution of an aerosolized powder determined by Anderson cascade impaction.

In brief, cascade impaction devices include a series of screens of decreasing pore size. The screens trap particles within a moving jet that passes through the impactor. The amount of particulate material (having particle sizes within a defined size range) that is trapped on each screen can be determined by washing the screen and measuring the amount of eluted material. Examples of cascade impactors, and their use, are described in Chapter 601 (Aerosols) of the Pharmacopoeia of the United States (26th Revision), the cited portion of which publication is incorporated herein by reference.

The powdered aminoglycoside antibiotic formulations useful in the practice of the present invention typically contain less than 15% by weight moisture, usually below about 11% by weight, and preferably below about 8% by weight.

In the practice of the present invention a therapeutically effective amount of an aerosol powder comprising an aminoglycoside antibiotic is administered by inhalation to a patient suffering from an endobronchial infection. A therapeutically effective amount of an aerosol powder contains sufficient aminoglycoside antibiotic to completely or partially inhibit the growth of susceptible bacteria in the lungs of the patient. As a representative example, for the aminoglycoside tobramycin therapeutically effective amounts are obtained by administering to a patient from once daily to three times a day, and in preferred aspects of the invention twice a day, an aerosol powder compositions comprising a dosage from about 90 mg to about 130 mg, more preferably from about 100 mg to about 120 mg, and most preferably from about 110 mg to about 115 mg of tobramycin (determined as free-base weight excluding the weight of counterion(s) that may be present).

The dosage of administered aminoglycoside, such as tobramycin, may be administered from a single container as a single unit dose, or it may be divided into multiple containers or units doses for sequential administration, depending of the inhalation device used for delivery of the antibiotic. For example, the administered dosage of aminoglycoside antibiotic may be divided into two to six unit doses, more preferably three to five unit doses and even more preferably four unit doses. In one representative embodiment a dosage for administration of 112 mg of tobramycin (determined as free-base weight excluding the weight of counterion(s) that may be present) is loaded into 4 separate #2 HPMC capsules at fill weights of 27 mg of tobramycin as free base per capsule.

The dry powder aerosol compositions of the invention are administered to a patient for a first treatment period of from 20 to 36 days, more preferably from 26 to 30 days, and even more preferably for about 28 days. This first treatment period is followed by a second non-treatment period wherein no aminoglycoside antibiotic is administered to the endobronchial system of the patient. In one aspect of the invention, the second non-treatment period will continue for about 20 to 36 days, more preferably from about 26 to about 30 days, and most preferably for about 28 days.

In one representative embodiment, the methods of the invention are used to treat cystic fibrosis patients for management of chronic *Pseudomonas aeruginosa* infections. In this aspect, the invention contemplates the treatment of a cystic fibrosis patient suffering from an endobronchial infection, comprising administering to endobronchial system of the patient a dry powder aerosol composition comprising from 110 to 115 mg of tobramycin antibiotic twice a day for a first treatment period of 28 days, providing a second non-treatment period of from 26 to 30 days wherein no tobramycin antibiotic is administered to the endobronchial system of the patient, and then repeating the first and second treatment periods. In this aspect of the invention, the 110 to 115 mg dosage of tobramycin may be divided into three to five unit doses, preferably into four unit doses, for sequential administration. Since cystic fibrosis patients tend to be chronically infected with *P. aeruginosa*, the cycle of treatment for the first treatment period followed by the second non-treatment period will typically be repeated a plurality or multiplicity of times, and may be continued indefinitely for long term management of endobronchial infections in the cystic fibrosis patient.

The aerosol powder typically comprises from 20% (by weight) to 90% (by weight) of aminoglycoside antibiotic. Thus, in some embodiments of the present invention the aerosol powder comprises from 30% (by weight) to 80% (by weight) of an aminoglycoside antibiotic. In some embodiments of the present invention the aerosol powder comprises from 40% (by weight) to 70% (by weight) of an aminoglycoside antibiotic. In this context, the percentage (by weight) of the aminoglycoside antibiotic refers to the amount of the free antibiotic, excluding the weight of counterion(s) that may be present.

Aerosol powders of the invention typically, but not necessarily, include at least one physiologically acceptable carrier. For example, the aerosol powder can include one or more excipients, and/or any other component that improves the effectiveness of the aminoglycoside antibiotic. Such excipients may serve simply as bulking agents when it is desired to reduce the active agent concentration in the powder which is being delivered to a patient. Such excipients may also serve to improve the dispersability of the powder within a powder dispersion device in order to provide more efficient and reproducible delivery of the active agent and to improve the handling characteristics of the active agent (e.g., flowability and consistency) to facilitate manufacturing and powder filling. In particular, the excipient materials can often function to improve the physical and chemical stability of the aminoglycoside, to minimize the residual moisture content and hinder moisture uptake, and to enhance particle size, degree of aggregation, surface properties (e.g., rugosity), ease of inhalation, and targeting of the resultant particles to the deep lung.

Pharmaceutical excipients and additives useful in the aminoglycoside compositions useful in the practice of the present invention include, but are not limited to, proteins, peptides, amino acids, lipids, polymers, and carbohydrates (e.g., sugars, including monosaccharides, di-, tetra-, and oligosaccharides; derivatized sugars such as alditols, aldonic acids, esterified sugars; and polysaccharides or sugar polymers), which may be present singly or in combination. Exemplary protein excipients include serum albumin such as human serum albumin (HSA), recombinant human albumin (rHA), gelatin, and casein. Representative amino acid/polypeptide components, which may also function in a buffering capacity, include alanine, glycine, arginine, betaine, histidine, glutamic acid, aspartic acid, cysteine, lysine, leucine, proline, isoleucine, valine, methionine, phenylalanine, and aspartame, although arginine is less preferred. Polyamino acids of the representative amino acids such as di-leucine and tri-leucine are also suitable for use with the present invention.

Carbohydrate excipients suitable for use in the invention include, for example, monosaccharides such as fructose, maltose, galactose, glucose, D-mannose, and sorbose; disaccharides, such as lactose, sucrose, trehalose, cellobiose; polysaccharides, such as raffinose, melezitose, maltodextrins, dextrans, and starches; and alditols, such as mannitol, xylitol, maltitol, lactitol, xylitol sorbitol (glucitol), and myoinositol.

The aminoglycoside compositions may also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, the aminoglycoside compositions useful in the practice of the invention may include polymeric excipients/additives such as polyvinylpyrrolidones, hydroxypropyl methylcellulose, methylcellulose, ethylcellulose, Ficolls (a polymeric sugar), dextran, dextrates (e.g., cyclodextrins, such as 2-hydroxypropyl-β-cyclodextrin, hydroxyethyl starch), polyethylene glycols, pectin, salts (e.g., sodium chloride), antioxidants, antistatic agents, surfactants (e.g., polysorbates such as "TWEEN 20" and "TWEEN 80", lecithin, oleic acid, benzalkonium chloride, and sorbitan esters), lipids (e.g., phospholipids, fatty acids), steroids (e.g., cholesterol), and chelating agents (e.g., EDTA). Other examples of pharmaceutical excipients and/or additives suitable for use in the aminoglycoside compositions are listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are herein incorporated by reference.

A presently preferred combination of excipients is lecithin and calcium chloride. Lecithin is a member of the phosphatidylcholine group of naturally-occurring phospholipids that act as surfactants in mammalian (including human) lungs.

The aminoglycoside compositions useful in the practice of the invention may include a dispersing agent for improving the intrinsic dispensability properties of the aminoglycoside powders. Suitable agents are disclosed in PCT applications WO 95/31479, WO 96/32096, and WO 96/32149, hereby incorporated in their entirety by reference. As described therein, suitable agents include water soluble polypeptides and hydrophobic amino acids such as tryptophan, leucine, phenylalanine, and glycine. Leucine and tri-leucine are particularly preferred for use according to this invention.

The solid state matrix formed by the aminoglycoside and excipient imparts a stabilizing environment to the aminoglycoside. The stabilizing matrix may be crystalline, an amorphous glass, or a mixture of both forms. Most suitable are dry powder formulations which are a mixture of both forms. For aminoglycoside dry powder formulations which are substantially amorphous, preferred are those formulations exhibiting glass transition temperatures ($T_g$) above about 35° C., preferably above about 45° C., and more preferably above about 55° C. Preferably, $T_g$ is at least 20° C. above the storage temperature. According to a preferred embodiment, the aminoglycoside compositions comprise a phospholipid as the solid state matrix as disclosed in WO 99/16419 and WO 01/85136, hereby incorporated in their entirety by reference.

Dry powder aminoglycoside compositions may be prepared by spray drying under conditions which result in a substantially amorphous glassy or a substantially crystalline bioactive powder as described above. Spray drying of the aminoglycoside-solution formulations is carried out, for example, as described generally in the "Spray Drying Handbook," 5th ed., K. Masters, John Wiley & Sons, Inc., NY, N.Y. (1991), and in WO 97/41833, the contents of which are incorporated herein by reference.

To prepare an aminoglycoside solution for spray-drying according to one embodiment of the invention, an aminoglycoside is generally dissolved in a physiologically acceptable solvent such as water. The pH range of solutions to be spray-dried is generally maintained between about 3 and 10, preferably 5 to 8, with near neutral pHs being preferred, since such pHs may aid in maintaining the physiological compatibility of the powder after dissolution of powder within the lung. The aqueous formulation may optionally contain additional water-miscible solvents, such as alcohols, acetone, and the like. Representative alcohols are lower alcohols such as methanol, ethanol, propanol, isopropanol, and the like. Aminoglycoside solutions will generally contain aminoglycoside dissolved at a concentration from 0.05% (weight/volume) to about 20% (weight/volume), usually from 0.4% to 5.0% (weight/volume).

The aminoglycoside-containing solutions are then spray dried in a conventional spray drier, such as those available from commercial suppliers such as Niro A/S (Denmark), Buchi (Switzerland), and the like, resulting in a stable, aminoglycoside dry powder. Optimal conditions for spray drying the aminoglycoside solutions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause deactivation of aminoglycoside in the sprayed material. Such temperatures are typically determined experimentally, although generally, the inlet temperature will range from about 50° C. to about 200° C. while the outlet temperature will range from about 30° C. to about 150° C.

Aminoglycoside dry powders may also be prepared by lyophilization, vacuum drying, spray freeze drying, super critical fluid processing, or other forms of evaporative drying or by blending, grinding, or jet milling formulation components in dry powder form. In some instances, it may be desirable to provide the aminoglycoside dry powder formulation in a form that possesses improved handling/processing characteristics, e.g., reduced static, better flowability, low caking, and the like, by preparing compositions composed of fine particle aggregates, that is, aggregates or agglomerates of the above-described aminoglycoside dry powder particles, where the aggregates are readily broken back down to the fine powder components for pulmonary delivery, as described, e.g., in U.S. Pat. No. 5,654,007, incorporated herein by reference. Alternatively, the aminoglycoside powders may be prepared by agglomerating the powder components, sieving the materials to obtain the agglomerates, spheronizing to provide a more spherical agglomerate, and sizing to obtain a uniformly-sized product, as described, e.g., in WO 95/09616, incorporated herein by reference. The aminoglycoside dry powders are preferably maintained under dry (i.e., relatively low humidity) conditions during manufacture, processing, and storage.

According to one embodiment, an exemplary powdered tobramycin formulation useful in the practice of the present invention may be made according to the emulsification/spray drying process disclosed in WO 99/16419 and WO 01/85136 cited above. Formulations according to such embodiments are engineered to comprise dry powder particles comprising at least 75% w/w tobramycin, preferably at least 85% w/w tobramycin, 2-25% w/w of a phospholipid, preferably 8-18% w/w, and 0-5% w/w of a metal ion such as calcium chloride. The particles of this embodiment generally have an MMAD of from 1 micron to 5 microns, and a bulk density of greater than 0.08 g/cm$^3$, preferably greater than 0.12 g/cm$^3$.

Another exemplary powdered tobramycin formulation useful in the practice of the present invention may be produced by creating an emulsion containing active tobramycin, 1,2-distearoyl-sn-glycero-3-phosphocholine (DSPC), CaCl$_2$ and perfluorooctyl bromide (PFOB). This feedstock emulsion is then sprayed through an atomizer nozzle, producing fine droplets. As the droplets dry, water and PFOB evaporate yielding phospholipid-based spherical particles with porous structure. These spheres are of low density and thus demonstrate favorable aerodynamic characteristics (e.g., the spherical particles have an aerodynamic diameter in the range of from 1 μm to 5 μm). Their high surface porosity also reduces particle-to-particle contact, decreasing the energy required for aerosol suspension.

The aerosol powder (comprising an aminoglycoside antibiotic) can be administered using a dry powder inhaler that uses a patient's (e.g., human's or animal's) inhaled breath to deliver the powdered aminoglycoside antibiotic formulation to the lungs. An example of a useful dry powder inhaler is the model T-326 inhaler (Nektar Therapeutics, 150 Industrial Road, San Carlos, Calif. 94070, U.S.A.). Other examples of useful dry powder inhalation devices are described in U.S. Pat. Nos. 5,458,135; 5,740,794; 5,775,320; and 5,785,049, each of which patents are incorporated herein by reference. When administered using a device of this type, the powdered medicament is contained in a receptacle having a puncturable lid or other access surface, preferably a blister package or cartridge, where the receptacle may contain a single dosage unit or multiple dosage units. Exemplary methods for filling large numbers of cavities with metered doses of dry powder medicament are described in U.S. Pat. No. 5,826,633, incorporated herein by reference.

Also suitable for delivering the aminoglycoside powders described herein are dry powder inhalers of the type described, for example, in U.S. Pat. Nos. 3,906,950, 4,013,075, 4,069,819, and 4,995,385, each of which patents are incorporated herein by reference, wherein a premeasured dose of aminoglycoside dry powder for delivery to a subject is contained within a capsule, such as a hard gelatin capsule. The size of the capsule, such as 00, 0, No. 1, or No. 3 sized capsules, depends, among other factors, upon the inhalation device used to administer the powders.

Other dry powder dispersion devices for pulmonarily administering aminoglycoside dry powders include those described, for example, in EP 129985, EP 472598, EP 467172, and U.S. Pat. No. 5,522,385, each of which patents are incorporated herein in their entirety by reference. Also suitable for delivering the aminoglycoside dry powders of the invention are inhalation devices such as the Astra-Draco "TURBUHALER". This type of device is described in detail in U.S. Pat. Nos. 4,668,218, 4,667,668, and 4,805,811, all of which are incorporated herein by reference.

Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in U.S. Pat. No. 5,388,572, incorporated herein by reference.

In view of the foregoing, it will be understood that a therapeutically effective amount of an aerosol powder (comprising an aminoglycoside antibiotic) can be administered from a single container, or from more than one container, disposed within a dry powder inhalation device. For example, a dry powder inhalation device may be loaded with a single container containing a therapeutically effective amount of an aerosol powder (comprising an aminoglycoside antibiotic), and the contents of the container are inhaled by a human or animal subject. Again by way of example, a dry powder inhaler may be loaded with multiple unit dose containers (e.g., 2, 3, or 4 containers), such as #2 HPMC capsules, that separately contain less than a therapeutically effective amount of an aerosol powder (comprising an aminoglycoside antibiotic), but which together contain a therapeutically effective amount of the aerosol powder. The dry powder inhaler discharges the contents of all of the containers disposed therein, and thereby provides the user with a therapeutically effective amount of the aerosol powder.

The aminoglycoside treatment regimen of the present invention may be used alone or in combination with one or more additional agents for the treatment of endobronchial infections, particularly infections by *P. aeruginosa*. In this aspect of the invention, the one or more additional agents for the treatment of endobronchial infections may be administered during the first treatment period of aminoglycoside treatment, during the second non-treatment period wherein no aminoglycoside antibiotic is administered to the endobronchial system of the patient, or during both the first and second treatment periods. In one embodiment of this aspect of the invention, the one or more additional agents for the treatment of endobronchial infections is administered during the second non-treatment period wherein no aminoglycoside antibiotic is administered to the endobronchial system of the patient. Suitable additional agents for the treatment of endobronchial infections include, for example, non-aminoglycoside antiinfective agents, such as monobactam, β-lactam, macrolide, fluoroquinolone and/or glycopeptide antibiotic compounds. For example, the non-aminoglycoside antiinfective agent may be aztreonam.

The emitted dose (ED) of the powdered aminoglycoside antibiotic formulations will generally be greater than 50%. More preferably, the ED of the powdered aminoglycoside antibiotic formulations useful in the practice of the present invention is greater than 70%, and is often greater than 80%. As used herein, the term "emitted dose" or "ED" refers to an indication of the delivery of dry powder from a suitable inhaler device after a firing or dispersion event from a powder unit, capsule, or reservoir. ED is defined as the ratio of the dose delivered by an inhaler device to the nominal dose (i.e., the mass of powder per unit dose placed into a suitable inhaler device prior to firing). The ED is an experimentally-determined amount, and is typically determined using an in-vitro device set up which mimics patient dosing. To determine an ED value, a nominal dose of dry powder (as defined above) is placed into a suitable dry powder inhaler, which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 50 mg, dry powder-containing #2 capsule placed into an inhalation device, if dispersion of the powder results in the recovery of 40 mg of powder on a tared filter as described above, then the ED for the dry powder composition is: 40 mg (delivered dose)/50 mg (nominal dose)×100=80%.

In yet other aspects, the invention provides for kits for use in the treatment of endobronchial infections in a patient, the kits comprising one or more doses of from 90 to 130 mg of a dry powder aminoglycoside antibiotic together with instructions for administration of a dosage to the endobronchial system of the patient using a dry powder inhalation device one to three times a day for a first treatment period of 20 to 36 days. In this aspect of the invention, the instructions may further provide that the first treatment period may be followed by a second non-treatment period wherein no aminoglycoside antibiotic is administered to the endobronchial system of the patient, and that the cycle of the first treatment period of aminoglycoside treatment followed by the second non-treatment period wherein no aminoglycoside antibiotic is administered to the endobronchial system of the patient may be repeated two or more times until the desired antibacterial effect is obtained, substantially as described herein. In the kits of the invention, the one or more doses may be contained in a single container as a single unit dose, or it may be divided into multiple containers or units doses for sequential administration, depending of the inhalation device used for delivery of the antibiotic. For example, the administered dosage of aminoglycoside antibiotic may be divided into two to six unit doses, more preferably three to five unit doses and even more preferably four unit doses. In one representative embodiment the kits of the invention contain dosages for administration of 112 mg of tobramycin (determined as free-base weight excluding the weight of counterion(s) that may be present) loaded into 4 separate #2 HPMC capsules at fill weights of 27 mg of tobramycin as free base per capsule.

The following examples merely illustrate the best mode now contemplated for practicing the invention, but should not be construed to limit the invention.

EXAMPLE 1

Preparation of Tobramycin Powder for Inhalation (TPI)

A tobramycin sulfate dry powder composition is prepared according to the following procedure. Sterile Water for Irrigation (SWFI) is heated above the gel to liquid crystal temperature (about 80° C.) of disteroyl phosphatidylcholine (DSPC). DSPC and calcium chloride dihydrate are then added to the heated water. The resulting lipid dispersion is mixed in an UltraTurrax T-50 (IKA Labortechnik) at 8,000 rpm for 5 min. Perfluorooctyl bromide (PFOB) is then added dropwise (15 ml/min) to the lipid dispersion under mixing. After the addition is complete the resulting PFOB-in-water emulsion is mixed for an additional 10 min at 10,000 rpm. Emulsification in the UltraTurrax produces droplets in the micron-size range. Tobramycin sulfate is then dissolved in the continuous phase of the emulsion and the resulting dispersion is used as the feedstock for spray drying. The feedstock is then spray dried to obtain a dry powder formulation having the composition set forth in Table 1 below.

TABLE 1

TPI Formulation.

| Component | Amount |
|---|---|
| Tobramycin | 63.1% w/w |
| Sulfate | 21.9% w/w |
| DSPC | 14.02% w/w |
| CaCl$_2$ | 0.98 w/w |

The powder is placed into a capsule filling station at a relative humidity of 10 to 15% and allowed to equilibrate for 10 minutes, and then filled into #2 HPMC capsules at a fill weight of 50 mg (27 mg of tobramycin as free base) per capsule.

EXAMPLE 2

This Example describes a clinical study that demonstrates that single dose administration of a tobramycin dry powder composition of the invention results in a more efficient delivery of tobramycin than administration of a tobramycin solution, while maintaining similar tobramycin pharmacokinetics.

Overall Study Design and Plan

The study was designed as a randomized, open-label, sequential-cohort, active-controlled, single-dose, dose-escalation study. In each sequential cohort, subjects were randomized in a 3:1 ratio to receive either a single dose of Tobramycin Powder for Inhalation (TPI) administered using a T-326 Inhaler (Nektar Therapeutics, San Carlos, Calif., USA), according to the dosing schedule shown below, or a single dose of 300 mg Tobramycin Solution for Inhalation (TOBI), aerosolized by a PARI LC PLUS™ jet nebulizer with a DeVilbiss PulmoAide™ compressor. Subjects were allowed to participate in one cohort only.

Escalation to the next TPI treatment cohort proceeded after review by a Data Monitoring Committee (DMC) of all treatment-emergent adverse events (AEs) and other safety results of the completed cohort and if neither of the following criteria were met: Three or more subjects within a cohort treated with TPI experience at least a 20% relative decline in $FEV_1$ within 30 minutes after the end of dosing; any TPI-dosed subject experienced a study drug-related Serious Adverse Event (SAE).

Experimental Treatment

A single dose of TPI was administered using the T-326 Inhaler:
Cohort 1: Two capsules of TPI (14 mg dosage strength of tobramycin as free base per capsule ("dosage strength"))
Cohort 2: Four capsules of TPI (14 mg dosage strength)
Cohort 3: Two capsules of TPI (28 mg dosage strength)
Cohort 4: Four capsules of TPI (28 mg dosage strength)
Cohort 5: Three capsules of TPI (28 mg dosage strength)
Control Treatment A single dose of TOBI at 300 mg/5 mL [preservative free tobramycin 60 mg/mL (excipient 5 mL of ¼ normal saline adjusted to a pH of 6.0±0.5)] aerosolized by a PARI LC PLUS jet nebulizer with a DeVilbiss PulmoAide compressor.

Up to 80 subjects of at least 6 years of age with a confirmed diagnosis of cystic fibrosis (CF) were randomized and treated in the study. Each cohort randomized 12 subjects to the TPI arm and 4 subjects to the TOBI arm for a total of 16 subjects per cohort.

Subjects were screened for eligibility 7 to 9 days prior to study drug administration. Subjects were evaluated for safety and for sputum and serum tobramycin concentrations at pre-dose, at 30 minutes, and at 1, 2, 4, 8, and 12 hours after the single dose of study drug was administered under supervision. A 7-day (±2 days) follow-up visit was conducted.

Discussion of Study Design, Including Choice of Control Group

The primary outcome measure for this study was the general safety and tolerability of the experimental treatment. To better assess this outcome, a 3:1 randomization scheme was chosen to maximize enrollment into the experimental treatment arm.

The active concurrent control for this study was 300 mg/5 mL TOBI delivered by a PARI LC PLUS jet nebulizer driven by a DeVilbiss PulmoAide compressor. TOBI is indicated for the management of cystic fibrosis patients with *P. aeruginosa*.

Inclusion Criteria for Selection of Study Population

Subjects were eligible to participate in the study if they met all of the following inclusion criteria.
Provide written informed consent and HIPAA authorization prior to the performance of any study-related procedure.
Male and female subjects ≥6 years of age at the time of screening.
Diagnosis of cystic fibrosis (CF) with documented sweat chloride ≥60 meq/L by quantitative pilocarpine iontophoresis test (QPIT) and/or genotype with two identifiable mutations consistent with CF, accompanied by one or more clinical features consistent with CF.
For female subjects who are ≥11 years of age or who have reached menarche: A negative serum pregnancy test. Sexually active females of childbearing age must agree to use contraception during the study period.
Able to expectorate sputum samples on command.
$FEV_1$≥40% of predicted value (calculated using Knudson equations based on gender, age, and height).
Able to comply with all protocol requirements.
Clinically stable in the opinion of the investigator.
Exclusion Criteria for Selection of Study Subjects
Subjects were excluded from participating in the study if they met any of the following exclusion criteria.
Administration of inhaled or intravenous aminoglycosides within 14 days prior to study drug administration and throughout the study period.
Administration of any investigational treatment within 14 days prior to study drug administration and throughout the study period.
Administration of loop diuretics within 7 days prior to study drug administration and throughout the study period.
Hemoptysis more than 60 cc at any time within 30 days prior to study drug administration.
Known local or systemic hypersensitivity to aminoglycosides or inhaled antibiotics.
Serum creatinine 2 mg/dl or more, BUN 40 mg/dl or more, or an abnormal urine analysis defined as 2+ or greater proteinuria.
Removal of Subjects from Therapy or Assessment
Subjects or their parents or legal guardians could withdraw their consent to participate in the study at any time without prejudice. The investigator could withdraw a subject if, in his or her clinical judgment, it was in the best interest of the subject or if the subject could not comply with the protocol. Whenever possible, the tests and evaluations listed for the termination visit were carried out.
If a subject failed to return for the necessary visits, an effort was to be made to determine the reason(s). This information was to be recorded on the appropriate case report form (CRF).
Randomized subjects who withdrew from the study without being dosed were replaced. Any randomized subject who withdrew after dosing was not replaced. The reason for withdrawal and the date of withdrawal were to be recorded on the CRF. The reasons for withdrawal were classified as follows:
Adverse event;
Protocol violation;
Lost to follow-up;
Withdrawal of consent;
Death;
Inappropriate enrollment;
Administrative reason;
Other, not specified above.
Treatments Administered Up to 80 subjects were randomized and treated. Each subject received a single dose of either the control treatment or the experimental treatment as listed below.

Experimental Treatment: Administered Using the T-326 Inhaler

Cohort 1: Two capsules of TPI (14 mg dosage strength)
Cohort 2: Four capsules of TPI (14 mg dosage strength)
Cohort 3: Two capsules of TPI (28 mg dosage strength)
Cohort 4: Four capsules of TPI (28 mg dosage strength)
Cohort 5: Three capsules of TPI (28 mg dosage strength)

Control Treatment

TOBI at 300 mg/5 mL [preservative free tobramycin 60 mg/mL (excipient 5 mL of ¼ normal saline adjusted to a pH of 6.0±0.5)] aerosolized by a PARI LC PLUS jet nebulizer with a DeVilbiss PulmoAide compressor.

Investigational Product Characteristics

TPI used in this study is a dry powder formulation of tobramycin and two excipients: 1,2 distearoyl-sn-glycero-3-phosphocholine (DSPC) and calcium chloride ($CaCl_2$). TPI was filled into individual size 2-hydroxyproplymethylcellulose (HPMC) capsules containing either 25 mg or 50 mg of powder. Two dosage strengths of tobramycin powder were used in the present study: 14 mg tobramycin per capsule and 28 mg tobramycin per capsule.

TOBI® Tobramycin Solution for Inhalation (300 mg/5 mL) is a sterile, non-pyrogenic, preservative-free antibiotic prepared for aerosolization. Each mL of study drug contains 60 mg tobramycin and 2.25 mg sodium chloride in sterile water for injection, pH 6.0±0.5.

Directions For Administration

Subjects randomized to the control treatment received 300 mg of TOBI® Tobramycin Solution for Inhalation at 60 mg/mL. TOBI® Tobramycin Solution for Inhalation was administered to subjects via a PARI LC PLUS jet nebulizer and DeVilbiss PulmoAide Compressor. The 300 mg dose of TOBI® Tobramycin Solution for Inhalation was supplied as a commercial ampoule of TOBI® Tobramycin Solution for Inhalation. Two 5 mL ampoules of study drug were provided in a foil pouch. Although this was a single-dose study, a foil pouch containing two 5-mL ampoules of study drug was provided to subjects in the event that there was accidental spillage of the study medication during preparation and set-up of the nebulizer and delivery system.

Subjects randomized to the experimental treatment received a single dose of TPI consisting of two or four capsules of 14 mg dosage strength or two, three, or four capsules of 28 mg dosage strength. TPI was administered to subjects via a T-326 Inhaler. TPI capsules were sealed in a double foil-wrapped, moisture-proof container and were to be administered within 30 minutes of opening the container. For cohorts 1, 2, and 3, only one T-326 Inhaler device was to be used to complete the single dose administration. For cohorts 4 and 5, the T-326 Inhaler device was to be replaced after the second capsule was administered; therefore, two T-326 Inhalers were to be used to complete the single dose administration for these cohorts.

Detailed instructions on the preparation and use of both the control and experimental treatment were provided to research staff at the study sites.

Method of Assigning Subjects to Treatment Groups

Eligible subjects were randomly assigned in a 3:1 ratio to either the experimental or control treatment group. Once the investigator or research coordinator confirmed that the subject met eligibility criteria, staff completed a randomization worksheet for the subject and received a subject number and treatment assignment via an Interactive Voice Response System (IVRS).

At the outset of the study, up to 80 subjects in five cohorts were expected to be randomized, 60 to the experimental treatment (12 subjects in each cohort) and 20 to the control treatment (4 subjects in each cohort).

Selection of Doses Used in the Study

The dose for the control treatment was the FDA-approved dose of 300 mg TOBI for the management of *P. aeruginosa* in CF patients 6 years of age and older. Using PK modeling, the systemic bioavailability of the 300 mg dose of TOBI delivered via the PARI LC PLUS jet nebulizer/DeVilbiss PulmoAide compressor was estimated to be 11.7% of the nebulized dose. The mean and standard deviation of the serum concentration of the 300 mg TOBI dose, one hour after inhalation, was 1.0±0.58 µg/mL, suggesting a wide range of deposition.

The dose for the experimental treatment was two or four TPI capsules containing 14 mg tobramycin/capsule; or two, three, or four TPI capsules containing 28 mg tobramycin/capsule.

Selection and Timing of Dose for Each Subject

Subjects were given a single dose of either 300 mg TOBI® Tobramycin Solution for Inhalation at 60 mg/mL or a single dose of TPI consisting of two or four capsules of 14 mg dosage strength, or two, three, or four capsules of 28 mg dosage strength. There was no restriction on the timing of dosing in relation to meals.

Blinding

The study was an open-label clinical investigation. The use of two different delivery systems makes blinding of the treatment identity impractical.

Prior and Concomitant Therapy

Additional supportive therapy was administered in accordance with standard practice at each study site. Medications listed in the exclusion criteria were not administered to the subject from the time of screening through the follow-up visit.

Subjects were allowed to use bronchodilators before taking the study drug. Bronchodilators were administered only to subjects who routinely used bronchodilators for clinical therapy. Routine use is defined as once or more daily for two weeks prior to screening. Subjects on short-acting bronchodilators were administered the medication 15 to 60 minutes prior to the initiation of the study drug. Subjects on long-acting bronchodilators took the medication as prescribed in the preceding 24 hours.

The use of the following drugs was prohibited: any form of aminoglycosides or any investigational treatment within 14 days prior to study drug administration and throughout the study period; loop diuretics within seven days prior to study drug administration and throughout the study period.

Treatment Compliance

The subject self-administered the single dose of study drug in the presence of the investigator or research coordinator. Reasons for any premature termination, interruption, or delay in study drug administration were recorded on the source documentation and CRF. Total study drug administration time was recorded on the source documentation and CRF.

Each subject (or parent/legal guardian if appropriate) in the care of the investigator provided written informed consent, including HIPAA authorization, and the subject assented (if appropriate) to participate in the study, before any study-related procedures were performed. Investigators screened subjects at visit 1, seven to nine days before day 1 (visit 2) study drug administration, to determine eligibility for enrollment. Investigators reviewed and recorded subjects' relevant medical history, including history of current disease and other pertinent respiratory history, baseline signs and symptoms, inhaled dry powder use and inhaled antibiotic use within 6 months before screening, and current medications and therapies ongoing at screening.

Investigators performed a screening physical examination of subjects, including measures of height, body weight, and vital signs. Vital signs included heart rate, respiratory rate, oral temperature, and sitting arterial blood pressure. Heart rate and respiratory rate were taken for 1 minute after the subject had rested for at least 10 minutes. Blood pressures were measured while the subject was seated after resting for at least 10 minutes.

All subjects whose regular medication regimen included routine use of short-acting bronchodilators for clinical therapy at least once or more daily for two weeks prior to screening were administered a bronchodilator 15 to 30 minutes before a screening spirometry test and 15 to 60 minutes before study drug administration. Subjects on long-acting bronchodilators took the medication as prescribed within 24 hours before study drug.

Subjects completed a routine spirometry test according to the 1994 American Thoracic Society guidelines to measure forced expiratory volume in 1 second ($FEV_1$), forced vital capacity (FVC), and mid-range forced expiratory flow rate ($FEF_{25-75}$), to document their ability to reliably perform spirometry, and to ensure that they met the inclusion requirement that $FEV_1$ equal or exceed 40% of the predicted value, calculated using Knudson equations based on gender, age, and height.

Subjects provided a blood sample for screening chemistry and hematology tests and a urine sample for dipstick proteinuria evaluation. Female subjects who were 11 years or older or who had reached menarche provided a urine sample for pregnancy testing.

Subjects who satisfied all inclusion and exclusion requirements were eligible to participate in the study and were randomized to treatments as described in the protocol. Randomized subjects were to return to the clinic 7 to 9 days later (visit 2) to receive study treatment and treatment-related procedures.

At visit 2, before administration of day 1 study treatments, all randomized subjects completed predose procedures, which included assessments of change in baseline symptoms, change in concomitant therapies, and measurement of vital signs. Investigators performed a repeat physical examination if any of the body systems were abnormal and clinically significant at screening or if the subject had any clinically significant change in health status from the time of screening. The urine dipstick test for proteinuria was to be repeated before dosing, if trace or 1+ at screening; serum chemistry and hematology were also to be repeated if abnormal at screening. Investigators performed a predose spirometry test (15 to 30 minutes after subjects' usual short-acting bronchodilator, if applicable) and collected serum and sputum samples for predose tobramycin assays.

Before administration of study treatments, TPI subjects currently using a short-acting bronchodilator either regularly or on demand could be pretreated with their short-acting bronchodilator at the discretion of the investigator. Subjects not currently using a short-acting bronchodilator could be pretreated with one if they had a 10% or greater relative decline in $FEV_1$ between the screening and pre-dose pulmonary function tests. Relative percent change from screening in $FEV_1$ was calculated as follows.

Relative % $FEV_1$ change from screening
=[(predose $FEV_1$–screening $FEV_1$)/screening $FEV_1$]×100

A single dose of study treatments was administered within 60 minutes after predose bronchodilator administration, if applicable, or spirometry, and subjects were evaluated for aerosol delivery and safety objectives of the protocol as described in following sections. At the time of dosing, subjects were instructed to sit upright, breathe normally, and use nose clips during inhalation of study treatment. The research coordinator recorded start and stop times for study treatment administration. If the subject experienced prolonged cough (greater than 10 seconds), the research coordinator stopped the timer and restarted it when the subject resumed treatment. For TPI subjects, the Investigator and/or research coordinator noted whether a rattling sound emanating from the inhaler was heard on the second inhalation of the study drug. Immediately after completing study drug administration, subjects rinsed their mouths with 30 mL of normal saline, gargled for 5 to 10 seconds, and expectorated the rinse; this rinse procedure was performed three times.

Subjects remained at the clinic to complete safety assessments for 12 hours after the start of administration of study treatments. Subjects were then discharged from the clinic and scheduled to return to the clinic for visit 3 follow-up on day 8 (±2 days). Flexible scheduling of follow-up visits due to subject constraints (the follow-up visit is designated as "day 8" throughout this Example was permitted). Slight deviations from the protocol schedule were considered to have minimal or no effect on the evaluation of study objectives.

During the day 8 follow-up visit, the research coordinator reviewed any changes in subjects' medical history, including concurrent illnesses, new or worsening adverse events, CF-associated symptoms, current medications and dosages, and over-the-counter medications. Subjects with clinically significant, study drug-related adverse events (AEs) were followed with repeated evaluations (either via phone or at clinic visits) until satisfactory resolution. The investigator performed a physical examination of the subject, measured height, weight, vital signs, and spirometry results, and collected blood and urine specimens for chemistry, hematology, and dipstick proteinuria tests.

Primary Aerosol Delivery Variable(s)

Estimation of the comparable dose of TPI to TOBI 300 mg/5 mL was based on evaluation of the aerosol delivery characteristics of the test treatment and the control treatment. Aerosol delivery characteristics of test and control treatments were determined on the basis of serum and sputum tobramycin concentrations over time, calculation of certain serum and sputum pharmacokinetic parameters as described in this Example, measurement of treatment administration time, and evaluation of T-326 Inhaler device and capsule performance.

Serum Tobramycin Concentrations

Blood samples were collected at predose and at 0.5, 1, 2, 4, 8, and 12 hours after the start of the first tidal breath during inhalation of study treatment. Samples were to be collected as close as possible to specified times and were considered to have been drawn on time if collected within ±2 minutes of the scheduled 0.5-hour posttreatment collection time and within ±10 minutes of scheduled times for the ensuing posttreatment collections. Samples collected outside these intervals were considered protocol deviations.

Serum was harvested and stored at −20° C. or below until analysis. Concentrations of tobramycin in serum were analyzed with a modified fluorescence polarization immunoassay (FPIA) method using the Abbott TDx®/TDxFLx® System. Samples were added directly to the dilution well of the sample cartridge. The net polarization was acquired by the TDx/TDxFLx apparatus. A weighted four-parameter logistic equation was used to calculate the concentrations of tobramycin. The concentrations of tobramycin were reported in terms of free base equivalents.

For assaying the subject samples of the study, calibration standards (0.05, 0.10, 0.40, 0.80, and 0.90 µg/mL) and quality control samples (0.10, 0.40, and 0.80 µg/mL) were prepared. The assay was completed in 6 runs.

The lower limit of quantitation was 0.05 µg/mL. The precision of the assay, as reflected by the CV of the quality control samples, was 4.9%, 5.7%, and 5.6% for the 0.10, 0.40, and 0.80 µg/mL samples, respectively. The accuracy of the method, reflected by the mean interassay recoveries of the quality control samples, was 103%, 103%, and 101% for the 0.10, 0.40, and 0.80 µg/mL samples, respectively. Overall, this method exhibited suitable accuracy and precision for pharmacokinetic analysis.

Calculation of serum pharmacokinetic parameters and estimation of the comparable dose of TPI are described in this Example.

Sputum Tobramycin Concentrations

Sputum samples were expectorated by subjects from a deep cough and collected before day 1 dosing (predose) and at 0.5, 1, 2, 4, 8, and 12 hours after the start of the first tidal breath during inhalation of study treatment. Sputum samples were collected as close as possible to specified times and within the same time windows as the serum collections. Samples collected outside these intervals were considered protocol deviations.

A sputum sample (minimum of 100 mg) was collected before the single dose of study treatment to determine the baseline tobramycin concentration.

Sputum samples were stored at −70° C. or below until analysis. The concentration of tobramycin was analyzed using a validated, reverse-phase, high-performance liquid chromatography (HPLC) method with ultraviolet detection.

Subject sputum samples were first liquefied with ⅕ normal sodium hydroxide and diluted with Tris buffer (20.0 g Trizma base/L). Sputum standard samples were prepared by spiking diluted pooled sputum from CF subjects with tobramycin to final concentrations of 0, 20, 40, 100, 200, 400, and 1000 µg/g of sputum. Assay quality control samples were prepared by spiking diluted pooled sputum to contain 40, 300, and 800 µg/g. The internal standard sisomycin (100 µL, 0.15 mg/mL in Tris buffer) was added to 100 µL of each standard, control, and subject sample, followed by 400 µL of acetonitrile and 50 µL of 2,4-dinitrofluorobenzene (0.17 g/mL). The sample reaction mixtures were heated in a dry-block heater for 1 h at 80° C. After addition of 600 µL of 60/40 acetonitrile/water (v/v), 50 µL was analyzed by HPLC.

Samples were injected onto a Waters Nova-Pak® C-18, 3.9×150 mm, 4 µm column connected to a Waters HPLC with 600E pump, 486 or 2487 ultraviolet detector ($\lambda$max=360 nm) and 717 Plus autosampler. The mobile phase consisted of 0.2% acetic acid in acetonitrile (39/61, v/v), pumped at a rate of 1.5 mL/min for 5 min, 2.0 mL/min for an additional 9 or 10 min, depending on the length of the run. Waters Millennium-32 C/S LC Software (version 3.20) was used to operate the Waters HPLC instruments as well as acquire raw data, process, compute, and report the analytical results. The ratio of the peak height of tobramycin to the internal standard sisomycin (PHR) was calculated. The assay was completed in 17 runs.

Retention time ranges of 3.8 to 4.1 min and 10.0 to 10.6 min were observed for tobramycin and sisomycin, respectively. A linear relationship existed between PHR and concentration from 20 to 1000 µg/g for sputum. The regression model was PHR=Bx+A (x=tobramycin concentration), weighted 1/x. The lower limit of quantitation was 20 µg/g. The concentrations of the standard samples were within 97 to 102% of the nominal concentration, with coefficients of variation (CV) not higher than 5.2%. The precision of the assay, as reflected by the CV of the quality control samples, was 5.2%, 3.9% and 2.0%, for the 40, 300, and 800 µg/g samples, respectively. The accuracy of the method, reflected by the interassay recoveries of the quality control samples, was 107%, 99%, and 97% for the 40, 300, and 800 µg/g quality control samples, respectively. Overall, this method exhibited suitable accuracy and precision for pharmacokinetic analysis.

Treatment Administration Time

Treatment administration time was defined as the length of time from the start of the subject's first inhalation to completion of treatment administration. Treatment administration was complete when the test T-326 Inhaler began to rattle and when the control PARI LC PLUS nebulizer began to sputter. The investigator noted, for TPI capsules, whether rattling was heard on the second breath by the subject, an indication that the capsule had been emptied.

If treatment administration was interrupted for any reason, the time of interruption and start and stop times of continued administration were to be recorded. If dosing was interrupted, total treatment administration time was not to include the duration of the interruption. If dosing was interrupted and either the stop time at interruption or the dose restart time was missing, treatment administration time was considered to be not calculable.

Inspection and Residual Tobramycin Analyses of Used T-326 Inhaler Devices and TPI Capsules Although not specified in the study protocol, used T-326 Inhaler devices and used TPI capsules were analyzed after use for performance evaluation.

Adverse Events

An adverse event (AE) is defined as any untoward medical occurrence in a clinical investigation subject administered a pharmaceutical product, at any dose, that does not necessarily have to have a causal relationship with this treatment. An AE could therefore be any unfavorable and unintended sign (including abnormal laboratory findings), symptom, or disease temporally associated with the use of a medicinal product, whether or not considered related to the medicinal product. This definition includes intercurrent illnesses or injuries, and exacerbation of pre-existing conditions. An unexpected AE is an event the nature or severity of which is not consistent with the applicable product information.

AEs may have been volunteered spontaneously by the subject or discovered as a result of general questioning by the investigator or research coordinator.

All AEs were to be monitored until resolution or, if the AE was determined to be chronic, a cause was identified. If an AE remained unresolved at the conclusion of the study, a clinical assessment was to be made by the investigator and medical monitor whether continued follow-up of the AE was warranted.

The severity of events reported on the AE CRF was determined by the investigator as follows:

Mild: No limitation of usual activities.

Moderate: Some limitation of usual activities.

Severe: Inability to carry out usual activities.

The relationship of the study treatment to an AE was determined by the investigator based on the following definitions:
Not Related: Exposure to the investigational product did not occur, or the occurrence of the AE is not reasonably related in time, or the AE is considered unlikely to be related to the investigational product.
Possibly Related: The study product administration and the AE were reasonably related in time, and the AE could be explained equally well by causes other than exposure to the investigational product.
Probably Related: The study treatment and the AE were reasonably related in time, and the AE was more likely explained by exposure to the study product than by other causes, or the investigational product was the most likely cause of the AE.

Serious Adverse Events (SAEs)
No SAEs were reported in this study.

Clinical Laboratory Tests
Laboratory tests to measure baseline hematology, serum chemistry, and dipstick proteinuria were performed at the time of screening and at the follow-up visit on day 8. At the dosing visit on day 1, blood urea nitrogen (BUN) and serum creatinine were measured 12 hours after the start of study drug administration. In addition, the urine dipstick test for proteinuria was repeated before dosing, if trace or 1+ at screening; serum chemistry and hematology were also repeated if abnormal at screening.

Hematology tests performed for this study included white blood cell count (WBC), red blood cell count (RBC), hemoglobin, hematocrit, differential, and platelet count.

Serum chemistry tests performed included sodium, potassium, chloride, bicarbonate, BUN, creatinine, glucose, calcium, phosphorus, gamma glutamyl transferase (GGT), alanine transaminase (ALT or SGPT), aspartate transaminase (AST or SGOT), alkaline phosphatase, lactic dehydrogenase (LDH), total bilirubin, direct bilirubin, indirect bilirubin, total protein, albumin, and serum human chorionic gonadotrophin (HCG).

Bronchospasm and Spirometry
Spirometry testing (forced expiratory volume in one second [$FEV_1$ in liters], forced vital capacity [FVC in liters], and forced expiratory flow rate during the middle two quarters of the forced vital capacity [$FEF_{25-75}$]) was performed before the day 1 single dose and at 30 minutes after completion of dosing to assess airway response to study treatments. A routine spirometry test was also performed at the day 8 follow-up visit.

The study protocol prospectively defined bronchospasm as a relative decline of 20% or more in $FEV_1$% predicted from predose to 30 minutes after the end of dosing. Subjects with a relative decline of 10% or more in $FEV_1$% predicted were also noted.

At 30 minutes after dosing, if the relative % $FEV_1$ decline was 20% or more, spirometry ($FEV_1$, FVC, and $FEF_{25-75}$) measurements were to be repeated according to a schedule defined by the investigator until the $FEV_1$ decrease was less than 10% (this was not done for subject 12/317, the only subject who experienced a 20% or greater decline in $FEV_1$ percent predicted). All instances of decline in $FEV_1$% predicted of 20% or more were to be recorded as AEs (this was not done for subject 12/317). Treatment with appropriate medications and further follow-up were at the discretion of the investigator.

Vital Signs
Vital signs were measured before the day 1 dose and at 30 minutes and 1, 4, 8, and 12 hours after the start of dosing and included sitting arterial blood pressure, heart rate, and respiratory rate taken after 10 minutes rest, and body temperature. Vital signs were also measured at the day 8 follow-up visit.

Physical Examinations
Physical examination of subjects was performed at the day 8 follow-up visit and consisted of physician review of subjects' general appearance, skin, lymph nodes, HEENT, lungs, cardiovascular, abdomen, extremities, musculoskeletal, neurologic, and genitourinary (optional) body systems.

Appropriateness of Measurements
The measures of efficacy used in this study are standard, i.e., widely used and generally recognized as reliable, accurate, relevant, and discriminatory between effective and ineffective agents. The measures of safety used in this study are standard clinical and laboratory procedures.

Pharmacokinetics
The concentration (C) versus time (t) data from sputum and serum tobramycin assays were analyzed by model-independent methods to obtain the pharmacokinetic parameters. The maximum concentration ($C_{max}$) and the time to maximum concentration ($t_{max}$) were obtained by inspection. The terminal rate constants ($\lambda_z$) were determined by log-linear regression of the terminal phase. The half-life was calculated as $t_{1/2} = \ln(2)/\lambda_z$. Concentrations below the lower limit of quantitation were treated as zero for all calculations. The areas under the sputum and serum concentration-time curves from time zero (predose) to 12 hours, AUC(0,12), was calculated by the trapezoidal rule. The AUC to infinity, AUC(0,∞), was calculated as AUC(0,12)+C(12)/$\lambda_z$ where C(12) is the concentration 12 h after the start of dosing.

All pharmacokinetic parameters were expressed as the mean±SD. A harmonic half-life was estimated as $$\overline{t_{1/2}} = \ln(2)/\overline{\lambda_z},$$

in which $\overline{\lambda_z}$ is the arithmetic mean of the terminal rate constants at each dose. The standard deviation of the harmonic mean half-life, $SD(\overline{t_{1/2}})$, was obtained as $$SD(\overline{t_{1/2}}) = \frac{\ln(2)}{\overline{\lambda_z}} \times \frac{SD(\overline{\lambda_z})}{\overline{\lambda_z}},$$

where $SD(\overline{\lambda_z})$ is the standard error of the mean terminal rate constant at each dose.

Estimation of the Comparable Dose of TPI to TOBI
A linear regression model was fitted for log AUC(0,12) vs. log(TPI dose) of TPI serum concentration data from all cohorts to estimate the comparable dose of TPI to TOBI. The comparable dose and the 95% confidence interval were determined by taking the inverse of the fitted regression line and the upper and lower 95% confidence bands at the mean log AUC(0,12) of TOBI data.

Monitoring
The study was conducted according to the principles of Good Clinical Practice (GCP).

Data Handling
Case report form data were entered in duplicate into a Clintrial® database.

Data quality control was performed using Procedural Language/Sequential Query Language (PL/SQL) and SAS® software version 8.2 or higher (SAS Institute, Cary, N.C.). Analysis was performed using SAS software version 8.2 or higher, based on a predefined analysis plan. The estimated overall database error rate was 0.022% with an upper 95% confidence limit of 0.157% (rounded). This upper confidence limit is below the chosen standard of 0.5%.

Statistical Methods and Determination of Sample Size
The objectives of this phase 1 study were to assess the safety of test TPI and control TOBI treatments and to estimate the dose of TPI that would produce a comparable pharmacokinetic profile to that of TOBI 300 mg/5 mL. There were no efficacy objectives defined for this study. All planned summaries and analyses were exploratory in nature. There were no planned statistical comparisons between TPI and TOBI treatment groups and no planned statistical hypothesis tests for differences between the two treatments. Due to the small number of subjects available for enrollment at each center, the Analysis Plan for the study prospectively specified that data were to be pooled across centers for analyses.

All summaries and analyses were produced for each of the six treatment groups. Unless otherwise specified, frequencies and percentages were calculated for categorical variables, and the number of non-missing values, mean, standard deviation, minimum, median, and maximum were calculated for continuous variables. All data recorded on CRFs were presented in individual subject data listings.

Three subject populations were defined.
All-Enrolled Population: subjects who were enrolled and randomized in the study.
Safety-Evaluable Population: subjects who were randomized and took all or part of the prescribed study drug.
Pharmacokinetic-Evaluable Population: subjects who were randomized and took all of the prescribed study drug.

Baseline and demographic characteristics were summarized for the all-enrolled subject population. Assessments of the pharmacokinetics of tobramycin were conducted using the pharmacokinetic-evaluable population. Estimation of the dose of TPI that provided systemic tobramycin exposure that was comparable to TOBI was undertaken on the TPI comparable dose-evaluable population. Analyses of all other variables were undertaken using the safety-evaluable population.

SAS version 8.2 was used for all analyses. Microsoft Excel was used for graphic display of study results.

Aerosol Delivery Analysis and Estimation of Comparable TPI Dose

All subjects who received the single dose treatment were included in the analysis and evaluation of aerosol delivery characteristics, which were characterized on the basis of sputum and serum tobramycin concentrations, estimated serum pharmacokinetic parameters, and treatment administration time.

Serum AUC(0,12) was used to estimate the comparable TPI dose to TOBI. A linear regression analysis with log AUC(0,12) as the dependent variable and log (TPI dose) as the independent variable was performed using the data from all TPI groups. The comparable dose of TPI was determined by taking the inverse of the fitted regression line at the mean log AUC(0,12) of TOBI serum tobramycin concentrations from the five combined TOBI cohorts.

Secondary Aerosol Delivery Analyses

The study protocol identified no secondary aerosol delivery variables.

Safety Analyses

All subjects who received a dose of study treatment were evaluable for safety based on AEs, change in pulmonary function, clinical laboratory results, vital signs, and physical examinations.

Evaluation of Adverse Events

Baseline symptoms and treatment-emergent adverse events (AE) were coded using the MedDRA thesaurus. The total incidence of individual treatment-emergent AEs (percent of subjects who experienced the event at least once during or after study treatment) was evaluated descriptively for any noteworthy differences between TPI and TOBI treatments. No statistical tests were planned. AEs were also summarized by severity (mild, moderate, severe) and drug relationship (unrelated, possibly related) for test and control treatments. For drug relationship evaluations, the classification, "possibly related", included individual AEs that were judged to be probably related, possibly related, and of unknown relationship to study treatment by the investigator.

Change in Pulmonary Function

Normal values have been developed for $FEV_1$, FVC, and $FEF_{25-75}$ (spirometry measurements) if subjects are free of pulmonary disease. These norms are commonly used in studies of subjects with pulmonary disease. Raw spirometry measurements were converted to normative percent predicted values using Knudson Equations, as described below. For each subject, the Knudson normative value for $FEV_1$, FVC, or $FEF_{25-75}$ is a linear combination of the subject age (years) and height (cm) using the following formula:

$$\text{Knudson Normative Value}=C_0+C_1\times\text{Height}+C_2\times\text{Age}$$

where the coefficients $C_0$, $C_1$, and $C_2$ are determined based on subject gender and age group.

Given a raw observed value from spirometry measurements and the Knudson normative value, the percent (%) predicted value is calculated by:

$$\text{\% predicted value}=(\text{Raw Observed Value}/\text{Knudson Normative Value})\times 100$$

Change and relative change in $FEV_1$% predicted ($FEV_1$%) from predose to 30 minutes postdose after the end of dosing were calculated using the following formulae:

$$\text{Change}=\text{Postdose } FEV_1\%-\text{Predose } FEV_1\%$$

$$\text{Relative change}=[(\text{Postdose } FEV_1\%-\text{Predose } FEV_1\%)\div\text{Predose } FEV_1\%]\times 100$$

A subject was defined as experiencing bronchospasm when the relative change from baseline was a decline of $\geq 20\%$.

Change and relative change, and the incidence of bronchospasm, were compared descriptively between treatment groups. Additionally, the following variables were derived and summarized similarly:
the incidence of subjects with a relative decline of 10% or more in $FEV_1$% predicted from predose to 30 minutes after the end of dosing
changes and relative changes in FVC % predicted and $FEF_{25-75}$% predicted from predose to 30 minutes after the end of dosing
changes and relative changes in $FEV_1$% predicted, FVC % predicted, and $FEF_{25-75}$% predicted from predose to the day 8 follow-up visit.

Other Safety Variables

Other safety variables including clinical laboratory results, vital signs, concomitant medications, medical procedures, physical examinations were summarized descriptively. Additionally, changes from baseline to end of study were calculated and summarized for laboratory data, vital signs, and spirometry measurements; in these calculations, the baseline value was the last available assessment prior to study dosing. Changes in the incidence of laboratory results that were below and above the respective normal ranges were also evaluated.

Determination of Sample Size

The sample size and the choice of parallel design were determined on the basis of clinical and practical rather than statistical power considerations. All analyses were considered exploratory and were undertaken using descriptive methods. No inferential statistical analyses were planned for this study.

Interim Analyses

At the end of each study cohort, summaries of key safety variables were produced and provided to the Data Monitoring Committee (DMC) to review and decide on dose escalation. The following results were listed by subject and summarized by treatment following completion of each cohort to support the deliberations by the DMC:

subject demography;
$FEV_1$ percent predicted before and after dosing and percent change;
serious adverse events;
treatment-emergent AEs;
respiratory system treatment-emergent AEs.

This interim analysis procedure was designed solely to support the review of safety and the decision about dose escalation by the DMC. No statistical tests of study data were planned, and no statistical alpha-level adjustments were required as a result of interim safety and dose escalation reviews.

Screening, Enrollment and Randomization of Subjects

A total of 97 subjects were screened for the study by the 15 investigators.

Ninety of the 97 screened subjects met entrance criteria and were enrolled (Table 2) and randomized to one of the six treatments. Seven of the 97 screened subjects did not meet study entry criteria and were not enrolled.

TABLE 2

Enrollment and Randomization by Site and Treatment

| Site | TPI Dosage Regimens | | | | | TOBI | Total subjects |
| | 2 × 14 mg | 4 × 14 mg | 2 × 28 mg | 3 × 28 mg | 4 × 28 mg | 300 mg | by site |
| --- | --- | --- | --- | --- | --- | --- | --- |
| 01 | 3 | 1 | | 2 | 1 | 3 | 10 |
| 02 | 3 | 2 m | 1 | 1 | | 1 | 8 |
| 03 | 3 | | 2 | | | 1 | 6 |
| 04 | | 2 | | 3 | 1 | 3 | 9 |
| 05 | | 2 | 1 | 2 | 2 | 1 | 8 |
| 06 | | 2 | 2 | 1 | 1 | | 6 |
| 07 | | | 1 | 1 | 2 | 1 | 5 |
| 08 | | | | | 2 | 1 | 3 |
| 09 | | 1 | 1 | 1 | 2 | 3 | 8 |
| 10 | | 1 | | 1 | | 1 | 3 |
| 11 | | | 1 | 1 | 2 | | 4 |
| 12 | 1 | | 1 | 1 | | 1 | 4 |
| 13 | | | 2 | | | 3 | 5 |
| 16 | 2 | 3 | 2 | 1 | 1 | 1 | 10 |
| 17 | | | 1 | | | | 1 |
| Total enrolled and randomized | 12 | 14 | 15 | 15 | 14 | 20 | 90 |

Withdrawal of Subjects Before Treatment

Three of the 90 enrolled subjects were withdrawn before treatment due to predose AEs and did not receive the single dose of study treatment (Table 2). Eighty-seven of the 90 subjects were dosed with study treatment.

TABLE 3

Subjects Enrolled But Withdrawn Before Study Treatment

| Treatment | Disposition | Reason Subject Did Not Receive Study Treatment |
| --- | --- | --- |
| 4 × 14 mg | Withdrawn before dose | Predose AE: wheezing. |
| 2 × 28 mg | Withdrawn before dose | Predose AE: cough aggravated. |
| 4 × 28 mg | Withdrawn before dose | Predose AEs: cough aggravated, laryngitis NOS, pyrexia. |

Study Completion

Eighty-six of 87 subjects who were dosed with study treatment completed the study. One of the 87 dosed subjects was withdrawn from the study due to treatment-emergent AEs.

One of the 86 completing subjects was dosed, but evaluation of returned capsules after the study revealed that the capsules had not been pierced by the T-326 Inhaler. Serum tobramycin concentrations in this subject were below quantifiable limits (BQL), confirming that the subject received no study treatment.

Data Sets Analyzed for Aerosol Delivery Evaluation

Eighty-six of the 90 enrolled subjects were randomized, were administered a single dose of study treatment, and were evaluable for safety objectives of the protocol. Three of the 90 subjects were withdrawn from the study due to AEs before they received study treatment and were excluded from safety evaluations. One additional subject did not receive any study treatment due to the failure of the T-326 Inhaler to pierce the treatment capsules and was excluded from safety evaluations.

TABLE 4

Subjects Not Evaluable for Safety Evaluations

| Treatment | Subject Disposition | Reason Subject Not Evaluable for Safety Objectives |
| --- | --- | --- |
| 2 × 14 mg | Completed | Subject received no study treatment: capsule was not pierced, and tobramycin was not detected in serum. |
| 4 × 14 mg | Withdrawn before dose | Predose AE: wheezing. |

TABLE 4-continued

Subjects Not Evaluable for Safety Evaluations

| Treatment | Subject Disposition | Reason Subject Not Evaluable for Safety Objectives |
|---|---|---|
| 2 × 28 mg | Withdrawn before dose | Predose AE: cough aggravated. |
| 4 × 28 mg | Withdrawn before dose | Predose AEs: cough aggravated, laryngitis NOS, pyrexia. |

Eighty-four of the 86 subjects who received study treatment were evaluable for pharmacokinetic objectives and estimation of the TPI dose considered to be pharmacokinetically comparable to the TOBI dose. Two of the treated subjects were excluded from pharmacokinetic and comparable dose evaluations.

TABLE 5

Dosed Subjects Not Evaluable for Pharmacokinetic Evaluations

| Treatment | Subject Disposition | Reason Subject Inevaluable for Pharmacokinetic Objectives |
|---|---|---|
| 2 × 28 mg | Completed | Did not receive full dose due to technical complications with T-326 Inhaler; one full capsule was returned to sponsor. |
| 4 × 28 mg | Withdrawn | Did not receive full dose due to AE mid-way through dosing, which led to withdrawal of consent and withdrawal from the study; insufficient number of serum samples. |

Subjects who received no study treatment were also not evaluable for pharmacokinetic evaluations.

Demographic Characteristics

Forty-three male and 47 female subjects, 7 to 50 years of age, diagnosed with cystic fibrosis, were enrolled in the study. Mean ages were similar among the treatment groups, ranging from 19.5 years in the TOBI group to 24.1 years in the TPI 2×14 mg group. Fifteen subjects were 7 to 12 years of age, 22 subjects were 13 to 17 years, and 53 subjects were 18 to 50 years of age.

Seventy-nine subjects were Caucasian, five subjects were Hispanic, three subjects were black, and three subjects were of other origins. Gender and race distributions were similar between TPI and TOBI treatment groups, although a small gender disparity was noted between TPI 4×14 mg and TOBI groups (TPI: 11 female, 3 male subjects; TOBI: 8 female, 12 male subjects). The effect of this imbalance on study results is uncertain.

On the average, TPI and TOBI subjects were comparable in height and weight at screening.

Other Baseline Characteristics

Enrolled subjects had documented laboratory (sweat chloride ≥60 mEq/L by quantitative pilocarpine iontophoresis test (QPIT) and/or genotype with two identifiable mutations) and clinical evidence consistent with a diagnosis of clinically stable cystic fibrosis. Medical history findings and signs and symptoms present before the start of the study were similar between the treatment groups.

Other inclusion and exclusion criteria were satisfied. Of note, four subjects experienced mild to moderate, persistent haemoptysis that was present before day 1 dosing. All subjects met the inclusion criterion of screening $FEV_1$ being 40% or greater of the predicted value based on sex, age, and height. The median $FEV_1$ percent predicted was similar for subjects in the six treatment groups (from 58.51% in the TPI 2×14 mg group to 82.40% in the TPI 3×28 mg group and 67.95% in the TOBI group). All but three subjects met the entry requirement to have a dipstick urine protein result of less than 2+; three subjects did not provide a urine sample at screening.

Thirty-nine of 90 enrolled subjects had received dry powder via inhalation within the 6 months before screening, ranging from 25% to 60% of subjects per treatment group. Sixty-seven of 90 subjects had received TOBI (between 40% and 100% of subjects per treatment group), none of the subjects had received other inhaled aminoglycosides, and 10 of the 90 subjects had received other inhaled antibiotics within the previous 6 months.

Thirty-six of the 90 enrolled (i.e., both TPI and TOBI subjects) subjects used a short-acting bronchodilator as a part of their standard CF treatment within 15 to 60 minutes before study treatment. In two instances, bronchodilator use was more than 60 minutes before administration of study treatment.

Measurements of Treatment Compliance

Compliance with the single-dose treatment administration requirements of the protocol was acceptable, as 86 of 90 enrolled subjects received study treatment (three subjects withdrew before dosing due to baseline symptoms, and one subject was dosed but received no treatment because the T-326 device did not puncture the treatment capsules). Four additional subjects had dosing non-compliance events as listed in Table 6.

TABLE 6

Subjects With Dosing Non-Compliance Events

| Treatment | Disposition | Dosing Non-Compliance Events |
|---|---|---|
| 2 × 28 mg | Completed | Capsule dropped; subject did not take inhalations from 1$^{st}$ capsule |
| 4 × 28 mg | Completed | Site used one T-326 Inhaler, instead of two Inhalers, for 4 × 28 mg capsules. High level (>45%) of TPI residual found in T-326 Inhaler due to improper dosing. |
| | Completed | Site used one T-326 Inhaler, instead of two Inhalers, for 4 × 28 mg capsules. |
| | Completed | Subject was instructed to take one complete breath from 1$^{st}$ TPI capsule, instead of two breaths. |

Serum Tobramycin Concentrations and Pharmacokinetic Parameters

As shown in FIG. 1, mean serum concentration-time profiles of tobramycin after administration of TPI and TOBI indicate that the drug is rapidly absorbed: median $t_{max}$ was 1 h in all treatments. The distribution of the drug appears to be very fast, and the levels declined in a monoexponential fashion, with average terminal half-lives ranging between 2.8 and 3.5 h. The values of the pharmacokinetic parameters of tobramycin after TOBI administration are consistent with previous studies.

Increases in the dose of TPI led to increases in the exposure to tobramycin, as evidenced by the increasing values of AUC (0,∞), AUC(0,12), and $C_{max}$ (Table 8). These increases were slightly less than proportional with dose).

Four subjects experienced cough, which caused an interruption in dosing. The interruptions were seen at TPI doses 4×14 mg, 3×28 mg, and 4×28 mg. In all evaluable subjects with cough, the values of AUC(0,∞), AUC(0,12), and $C_{max}$ were within the range of other subjects in their dosing group who completed dosing without interruption.

No differences in exposure to tobramycin, as measured by AUC and $C_{max}$, were detected between subjects receiving 4×14 mg manual-fill capsules vs. 2×28 mg automatic-fill capsules (P>0.5). Therefore, the bioavailability of the hand- and automatic-fill capsules was comparable, and these two groups were consolidated.

In general, there was a weak negative correlation between the percentage of powder left in the device and AUC(0,∞) (r=−0.22, P=0.0771), AUC(0,12) (r=−0.23, P=0.0707), and $C_{max}$ (r=−0.22, P=0.0838). Lower exposures were associated with higher residual amounts of TPI in the device. One of the subjects in the 4×28 mg TPI dosing group (subject 04/409) had more than 45% residual powder in the device and had exposures of tobramycin that were among the lowest in his treatment group.

There were no significant correlations between change from baseline in $FEV_1$ and serum AUC and $C_{max}$ [for TPI subjects: AUC(0,∞) (P=0.9838), AUC(0,12) (P=0.9990), and $C_{max}$ (P=0.9110); for TOBI subjects: AUC(0,∞) (P=0.5216), AUC(0,12) (P=0.4337), and $C_{max}$ (P=0.3878)].

Sputum Tobramycin Concentrations and Pharmacokinetic Parameters

Figure 4:
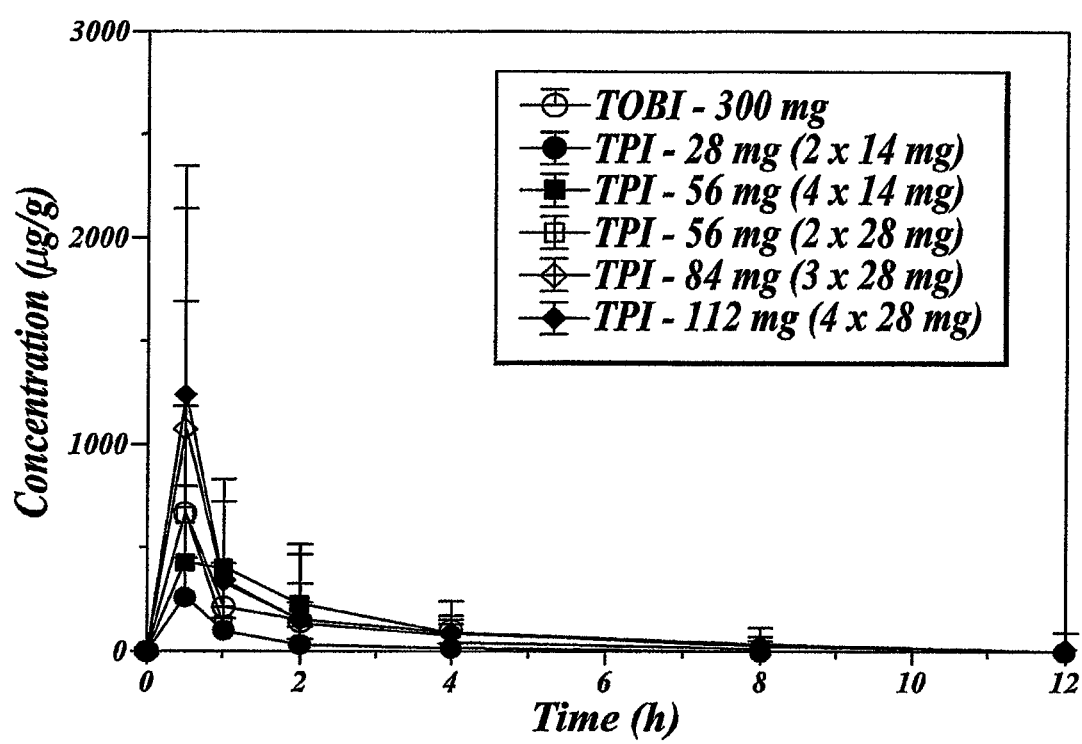
FIG. 4 shows the average concentration of tobramycin in sputum of subjects who had received a defined dosage of TOBI or TPI.

After administration of TPI and TOBI, maximum concentrations in sputum were achieved on average at 30 min (FIG. 4), declining thereafter with an average half-life of 0.8 to 2.2 h (Table 8).

The variability in pharmacokinetic parameters was higher in sputum, as compared to serum. In addition to the inherent variability in sputum-derived pharmacokinetic parameters,

TABLE 7

Selected Pharmacokinetic Parameters of Tobramycin in Serum After Administration of TOBI (300 mg) and TPI (28 mg, 56 mg, 84 mg, and 112 mg)

| Parameter | TOBI 300 mg | TPI 2 × 14 mg | TPI 4 × 14 mg | TPI 2 × 28 mg | TPI 3 × 28 mg | TPI 4 × 28 mg |
|---|---|---|---|---|---|---|
| AUC(0, ∞) (µg h/mL) | 5.3 ± 2.6 | 1.7 ± 0.6 | 3.1 ± 0.8 | 2.9 ± 1.2 | 4.1 ± 1.5 | 5.1 ± 2.0 |
| AUC(0, 12) (µg h/mL) | 4.8 ± 2.5 | 1.3 ± 0.6 | 2.8 ± 0.9 | 2.5 ± 1.2 | 3.5 ± 1.3 | 4.6 ± 2.0 |
| $C_{max}$ (µg/mL) | 1.04 ± 0.58 | 0.33 ± 0.09 | 0.56 ± 0.23 | 0.50 ± 0.21 | 0.70 ± 0.33 | 1.02 ± 0.53 |
| $t_{max}^a$ (h) | 1 (0.5-2) | 1 (0.5-2) | 1 (0.5-1) | 1 (0.5-2) | 1 (1-2) | 1 (0.5-2) |
| t½ (h) | 3.0 ± 0.8 | 2.8 ± 1.1 | 3.5 ± 0.8 | 3.3 ± 0.8 | 3.4 ± 1.0 | 3.1 ± 0.4 |
| n PK | 20 | 11 | 13 | 13 | 15 | 12 |
| n total | 20 | 12 | 13 | 14 | 15 | 13 |

[a]median (range). Except for number of subjects in last 2 rows, other entries are mean ± standard deviation.

Comparable Dose Analysis of TPI and TOBI

Figure 2:
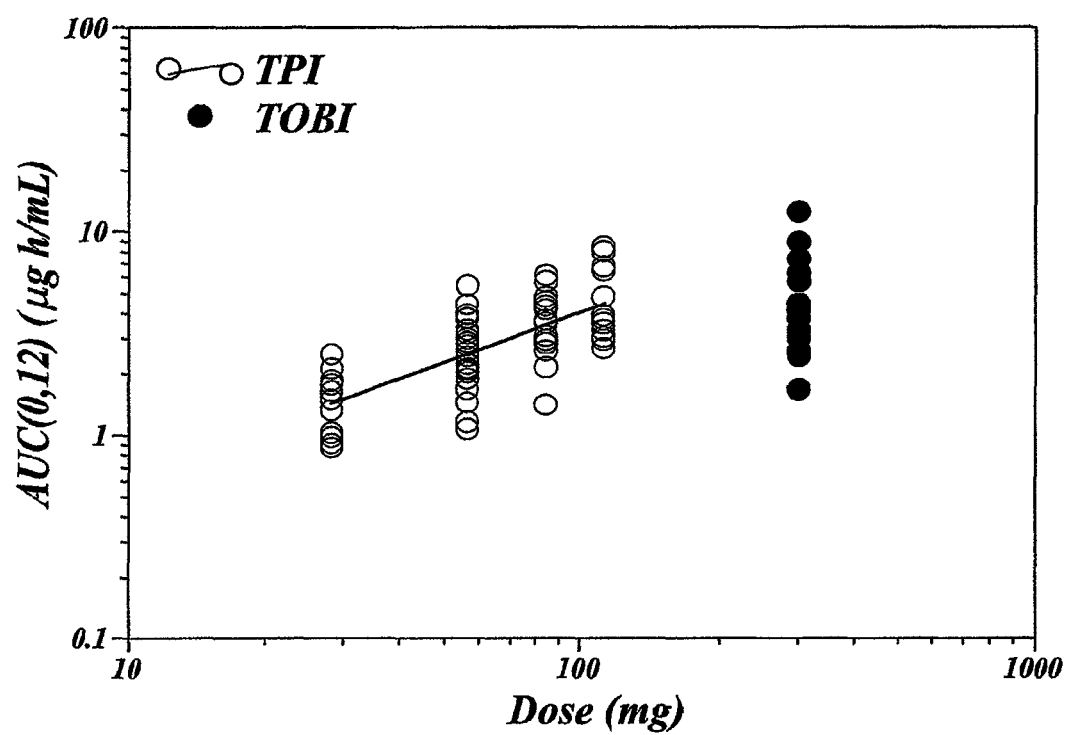
FIG. 2 shows a plot of dosage of Tobramycin Powder for Inhalation. (TPI) and Tobramycin Solution for Inhalation (TOBI) versus Area Under the Curve (AUC) (0,12).
Figure 3:
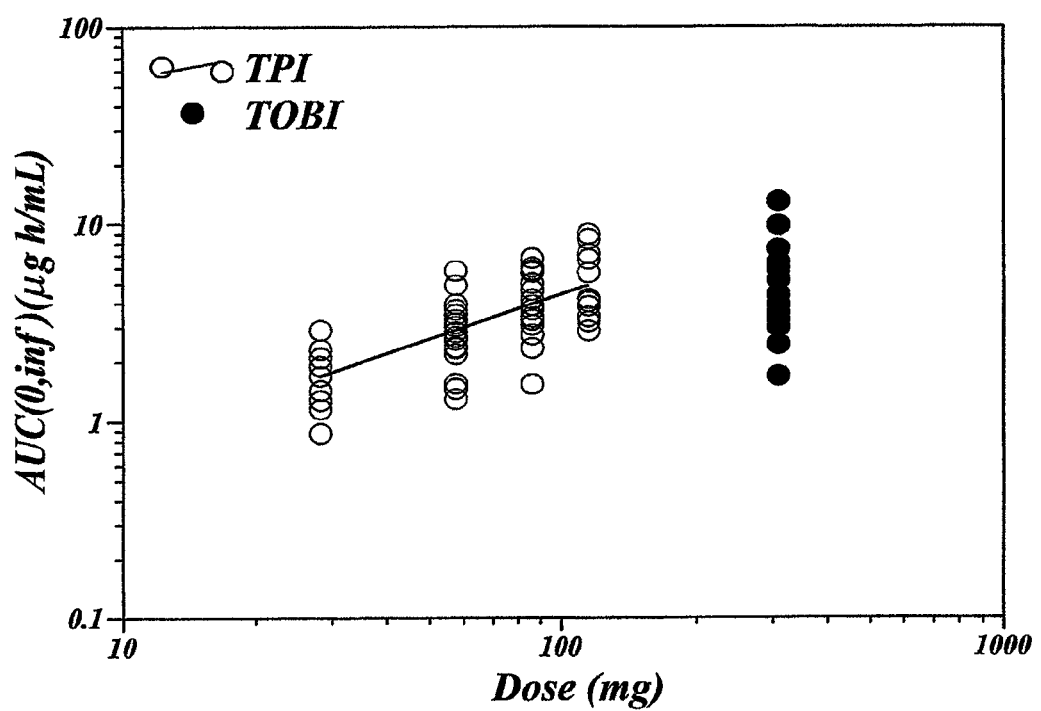
FIG. 3 shows a plot of dosage of TPI and TOBI versus AUC $(0,\infty)$.

The exposures achieved after administration of TOBI 300 mg were very similar to that seen after administration of 4×28 mg capsules of TPI (FIGS. 2 and 3). When the AUC(0,12) data from all cohorts was examined as a function of dose (FIG. 2), the results indicate that a dose of 115 mg of TPI would produce a mean AUC(0,12) similar to TOBI. When AUC(0,∞) was considered (FIG. 3), a dose of 112 mg would be expected to achieve a similar AUC(0,∞) to TOBI. Based on these results, it appears that four capsules of 28 mg of TPI (total close of 112 mg) would produce systemic exposure very close to that of TOBI.

some subjects were unable to produce sputum on demand (no more than three subjects per group with a missing sputum sample at any one time). This would have an impact on the calculation of exposure measurements: AUC(0,∞), AUC(0, 12), and $C_{max}$. As a consequence, while there is a trend of increasing exposure in sputum with increases in dose, dose proportionality based on sputum levels could not be confirmed.

TABLE 8

Selected Pharmacokinetic Parameters of Tobramycin in Sputum after Administration of TOBI (300 mg) and TPI (28 mg, 56 mg, and 112 mg)

| Parameter | TOBI 300 mg | TPI 2 × 14 mg | TPI 4 × 14 mg | TPI 2 × 28 mg | TPI 3 × 28 mg | TPI 4 × 28 mg |
|---|---|---|---|---|---|---|
| AUC(0, ∞) (µg h/g) | 1302 ± 1127 | 390 ± 139 | 1714 ± 1173 | 855 ± 469 | 2044 ± 1334 | 1740 ± 809 |
| AUC(0, 12) (µg h/g) | 974 ± 1143 | 261 ± 168 | 1195 ± 1224 | 652 ± 421 | 1340 ± 1320 | 1307 ± 978 |
| $C_{max}$ (µg/g) | 737 ± 1028 | 258 ± 194 | 515 ± 421 | 574 ± 527 | 1092 ± 1052 | 1048 ± 1080 |
| $t_{max}^a$ (h) | 0.5 (0.5-2.0) | 0.5 (0.5-0.5) | 0.5 (0.5-1.0) | 0.5 (0.5-4.0) | 0.5 (0.5-2.0) | 0.5 (0.5-1.0) |
| t½ (h) | 1.7 ± 1.6 | 0.9 ± 0.8 | 1.8 ± 0.9 | 1.3 ± 1.5 | 0.8 ± 0.8 | 2.2 ± 1.7 |
| n PK[b] | 20 | 11 | 12 | 13 | 15 | 11 |
| n total | 20 | 12 | 13 | 14 | 15 | 13 |

[a]median (range). Except for number of subjects in last 2 rows, other entries are mean ± standard deviation.
[b]n may be different for different parameters. The maximum number of subjects used in any single analysis is listed.

Study Drug Administration Time

Drug administration time averaged nearly 16 minutes in TOBI subjects (Table 9). By comparison, administration time for two capsules of TPI averaged 1.7 and 2.5 minutes for the 2×14 mg and 2×28 mg doses, respectively. Administration times averaged 4.2, 4.5, and 4.9 minutes for TPI 4×14 mg, 3×28 mg, and 4×28 mg doses, but in these cohorts a second device was unpacked and utilized for dosing of the third and fourth capsules, respectively. Thus, TPI administration time increased primarily as the number of capsules increased and, secondarily, as the dosage strength increased.

TABLE 9

Study Drug Administration Time

| Parameter | TOBI 300 mg (N = 20) | TPI 2 × 14 mg (N = 11) | TPI 4 × 14 mg (N = 13) | TPI 2 × 28 mg (N = 14) | TPI 3 × 28 mg (N = 15) | TPI 4 × 28 mg (N = 13) |
|---|---|---|---|---|---|---|
| Inhalation Time (min): Mean ± SD | 15.8 ± 4.0 | 1.7 ± 0.6 | 4.2 ± 1.4 | 2.5 ± 1.1 | 4.5 ± 1.1 | 4.9 ± 1.8 |

Evaluation of T-326 Inhaler and TPI Capsule Performance

All but two TPI capsules were administered as required (exception: $3^{rd}$ and $4^{th}$ capsules for one subject in the TPI 4×28 mg group). Rattling was heard on the second breath in 85% or more of the capsules.

There were no device failures reported by the sites or upon inspection by the Nektar analysts. The sum of the residual tobramycin in the subjects' inhaler(s) and capsules averaged 10.5% of the nominal dose. This analysis included subject 04/409, who had more than 45% residual powder in the device due to improper dosing, so more than likely, the actual amount of residual powder in the device was less.

Handling of Dropouts or Missing Data

During the study, three randomized subjects withdrew before they received study treatment due to predose AEs. Another randomized subject completed the study but was later found to have not inhaled study treatment because both TPI capsules were not pierced. Screening and enrollment continued until these subjects were replaced; replacement subjects were assigned the next available subject number in the randomization code.

One subject withdrew prematurely from the study. No last-result-carried-forward (LRCF) strategy was employed in the analyses to account for the early withdrawal.

Tobramycin concentrations below the lower limit of quantitation were treated as zero for all calculations.

Use of an "Aerosol Delivery Subset" of Subjects

The protocol indicated that subjects who were randomized and who took the complete dose of study treatment were evaluable for pharmacokinetics. As the study proceeded, unanticipated dosing and TPI capsule status issues led to revision of the evaluability criteria for pharmacokinetics. A total of six subjects were excluded from pharmacokinetic and comparable dose analyses (four subjects received no study treatment, and two subjects did not receive the full dose of study treatment). Eighty-four subjects were evaluable for pharmacokinetic and comparable dose evaluations.

All 86 enrolled subjects who were administered study treatments by inhalation were included in the evaluation of study treatment administration time and in the evaluation of residual tobramycin in capsules and T-326 Inhalers.

Active-Control Studies Intended to Show Equivalence

The study was not designed or powered to show clinical or pharmacokinetic equivalence between the test product and the control.

Examination of Subgroups

The following subgroup analyses were performed on dose-normalized serum exposure (AUC(0,12), AUC(0,∞), and $C_{max}$) of tobramycin after administration of TPI:
  subjects less than 12 years old vs. subjects 12 and older (P>0.4);
  previous dry powder users vs. nonusers (P>0.8);
  males and females (P>0.1);
  body weight (P>0.2).

None of these variables appeared to influence the exposure of tobramycin.

The exposure of tobramycin, as measured by AUC and $C_{max}$, in TPI subjects (N=27) using bronchodilators from 15 to 60 minutes after dosing was slightly higher than in subjects not using them (N=37). AUC(0,∞), AUC(0,12), and $C_{max}$ values were 19% (P=0.0685), 27% (P=0.0240), and 38% (P=0.0038) higher. Bronchodilator use may increase the amount of the tobramycin that eventually reaches systemic circulation, perhaps by an increase in the amount deposited in the lungs.

Aerosol Delivery Summary

Mean serum concentration-time profiles of tobramycin after administration of TPI and TOBI indicate that the drug is rapidly absorbed: $t_{max}$ was 1 hour in all treatments. The distribution of the drug appears to be very fast, and the levels declined in a monoexponential fashion, with average terminal half-lives ranging between 2.8 and 3.5 hours. The values of the pharmacokinetic parameters of tobramycin after TOBI administration are consistent with previous studies.

Increases in the dose of TPI led to increases in the exposure to tobramycin, as evidenced by the increasing values of AUC (0,∞), AUC(0,12), and $C_{max}$. These increases were slightly less than proportional to dose. No differences in exposure to tobramycin were detected between subjects receiving 4×14 mg manual-fill capsules vs. 2×28 mg automatic-fill capsules. Therefore, these two groups were consolidated for the comparable dose analyses. In general, there was a weak negative correlation between the percentage of powder left in the device and AUC(0,∞) (P=0.0707), AUC(0,12) (P=0.0771), and $C_{max}$ (P=0.0838). There were no significant correlations between changes in $FEV_1$ from baseline and AUC(0,∞) (P=0.9838), AUC(0,12) (P=0.9990), and $C_{max}$ (P=0.9110).

The exposures achieved after administration of TOBI 300 mg were between the exposures seen after administration of 3×28 mg and 4×28 mg capsules of TPI. Based on the results, it appears that four capsules of 28 mg of TPI (total dose of 112 mg) produce the closest systemic exposure to TOBI.

Subgroup analyses in TPI subjects showed that age, previous dry powder use, sex, and body weight did not influence the exposure to tobramycin in TPI, indicating that the pharmacokinetics of tobramycin is similar in these TPI subgroups. The exposure to tobramycin in TPI subjects using bronchodilators (N=27) was slightly higher on the average than in TPI subjects not receiving bronchodilators (N=37).

After administration of TPI and TOBI, maximum concentrations in sputum were achieved on average at 30 min, and average estimates of half-life ranged from 0.8 to 2.2 hours.

The variability in pharmacokinetic parameters was higher in sputum than in serum.

Drug administration time averaged nearly 16 minutes in TOBI subjects. By comparison, administration time for two capsules of TPI averaged 1.7 and 2.5 minutes for the 2×14 mg and 2×28 mg doses, respectively; administration times averaged 4.2, 4.5, and 4.9 minutes for TPI 4×14 mg, 3×28 mg, and 4×28 mg doses. Thus, TPI administration time increased primarily as the number of capsules increased and, secondarily, as the dosage strength increased.

Extent of Exposure

Eighty-six of 90 enrolled subjects received a single dose of study treatments, as summarized below.

12 subjects received up to 28 mg of TPI in a 2×14 mg single dose 13 subjects received up to 56 mg of TPI in a 4×14 mg single dose 14 subjects received up to 56 mg of TPI in a 2×28 mg single dose 15 subjects received up to 84 mg of TPI in a 3×28 mg single dose 13 subjects received up to 112 mg of TPI in a 4×28 mg single dose 20 subjects received up to 300 mg of TOBI in 5 mL single dose of a 60 mg/mL solution Brief Summary of Adverse Events More TPI subjects (40 of 66 subjects, 60.6%) than TOBI subjects (6 of 20, 30.0%) experienced treatment-emergent AEs during or after administration of single-dose study treatments. The percent of subjects with any AE was similar among the TPI dose levels (TPI 2×14 mg=45%; 4×14 mg=54%, 2×28 mg=64%, 3×28 mg=67%, 4×28 mg=69%); sample sizes were too small to determine whether a trend was present for increasing any-AE incidence with increasing TPI dose. All treatment-emergent AEs were mild or moderate in intensity.

One TPI 4×28 mg subject experienced moderate cough and sputum increased on day 2 which persisted and led to hospitalization on the eighth day after the single-dose study treatment was administered. Therefore, on day 8 after the subject completed the study, these AEs were determined to be SAEs. Neither of these SAEs, which occurred in the same subject, was considered related to TPI treatment. Another TPI 4×28 mg subject experienced the non-serious AEs of moderate, probably-related cough aggravated, dysgeusia, and lacrimation increased that caused study drug administration to be interrupted and then stopped; the subject then withdrew consent and was withdrawn from the study. Four subjects experienced non-serious AEs of coughing during inhalation of TPI that led to a modification, interruption, or delay in dosing (one subject each at TPI 4×14 mg and 4×28 mg and two subjects at 3×28 mg); each AE was considered to be probably related to TPI treatment by the investigator.

AEs experienced by the largest number of TPI subjects were cough or cough aggravated (13 of 66 subjects=19.7%; 12 of the 13 TPI subjects previously reported cough as a baseline symptom before the start of study treatment); dysgeusia (11 subjects, 16.7%); pharyngitis, haemoptysis, and rhinorrhea (4 subjects, 6.1% each); sputum increased, crackles lung, lacrimation increased, abdominal pain upper, dizziness, headache NOS, and throat irritation (3 subjects, 4.5% each). The incidence of cough, cough aggravated, and dysgeusia increased slightly with increasing TPI dose, but no conclusive trend in the incidence of any individual AE was observed in the data. By comparison, no more than one TOBI subject experienced any AE. TOBI subjects experienced no cough, cough aggravated, or dysgeusia. However, most subjects dosed with TOBI (17 of 20, 85%) received TOBI as part of their usual therapy.

The investigators considered most instances of cough and cough aggravated, all instances of dysgeusia, and most instances of haemoptysis and throat irritation to be possibly or probably related to TPI treatment. By comparison, single instances of chest tightness, herpes simplex, eosinophil count increased, dry throat, pharyngitis, sputum increased, and sputum viscosity increased were considered related to TOBI treatment.

Treatment-Emergent Adverse Events: All Causes

Forty of 66 TPI subjects and six of 20 TOBI subjects experienced treatment-emergent AEs during or after treatment. The percent of subjects with any AE was similar among the TPI dose levels. All treatment-emergent AEs were mild or moderate in intensity.

AEs experienced by the largest number of TPI subjects were cough or cough aggravated (13 of 66 subjects=19.7%); dysgeusia (11 subjects, 16.7%); pharyngitis, haemoptysis, and rhinorrhea (4 subjects, 6.1% each); sputum increased, crackles lung, lacrimation increased, abdominal pain upper, dizziness, headache NOS, and throat irritation (3 subjects, 4.5% each).

No more than one TOBI subject experienced any AE. TOBI subjects experienced no cough, cough aggravated, or dysgeusia.

Treatment-Emergent Adverse Events Considered Related to Treatments

Twenty-four of 66 TPI subjects (36.4%) and 2 of 20 TOBI subjects (10%) had AEs that were considered to be possibly or probably related to treatments by the investigators (Table 12). The investigators considered most instances of cough and cough aggravated (10 of 66 TPI subjects=15.2%) and all instances of dysgeusia (16.7%) to be possibly or probably related to TPI treatment (Table 11). Haemoptysis and throat irritation (both 4.5%) and lacrimation increased (3.0%) were also considered related to TPI treatment. By comparison, single instances of chest tightness, herpes simplex, eosinophil count increased, dry throat, pharyngitis, sputum increased, and sputum viscosity increased were considered related to TOBI treatment.

Other Serious Adverse Events

One TPI 4×28 mg subject experienced SAEs on day 2 (moderate cough and sputum increased) that led to hospitalization for exacerbation of CF lung disease on the eighth day after the single-dose study treatment. Neither of these SAEs, which occurred in the same subject, was considered related to TPI treatment.

Withdrawal of Subjects from the Study Due to Treatment-Related Adverse Events

One TPI 4×28 mg subject experienced moderate cough aggravated, dysgeusia, and lacrimation increased that caused study drug administration to be interrupted and then stopped, and the subject was withdrawn from the study. Each AE was considered to be probably related to TPI treatment by the investigator.

Dose Interventions Due to Treatment-Related Adverse Events

Four subjects experienced coughs that led to a modification, interruption, or delay in dosing (one subject each at TPI 4×14 mg and 4×28 mg and two subjects at 3×28 mg. Each AE was considered to be probably related to TPI treatment by the investigator.

TABLE 10

Dose Interventions Due to Adverse Events

| Treatment (Sex/Age)[b] | Study Day of AE[a] | Adverse event[a] | Dose interrupt[a] | SAE[a] | Subject withdrew[c] | Drug related[a] |
|---|---|---|---|---|---|---|
| TPI 4 × 14 mg (F/11) | 1 | Cough aggravated | Modified | No | No | Probable |
| TPI 3 × 28 mg (F/13) | 1 | Cough | Modified | No | No | Probable |
| (F/25) | 1 | Cough | Modified | No | No | Probable |
| TPI 4 × 28 mg (F/22) | 1 | Cough aggravated, throat irritation | Modified | No | No | Probable |

Analysis and Discussion of Deaths, Other Serious Adverse Events, and Other Significant Adverse Events No deaths were reported in this study. The only SAEs were moderate cough and sputum increased reported by a single subject on day 2, leading to hospitalization on day 8 after the subject completed the study; these events were considered unrelated to study treatment. Five TPI subjects developed moderate cough or cough aggravated within minutes after inhalation of TPI, which led one subject (who also had dysgeusia and increased lacrimation) to withdraw from the study and four subjects to interrupt dosing. All subjects reported baseline respiratory symptoms, and, of those who reported cough as an AE, all but one also noted it as a baseline symptom. These AEs resolved within 5 to 35 minutes with no or minimal intervention. The four latter subjects restarted and successfully completed dosing within minutes of the original interruptions. These AEs were probably related to the underlying bronchial irritability that often accompanies cystic fibrosis, although the investigator considered each event to be probably related to study drug administration. Thus, in this study, TPI at each dose level and TOBI 300 mg/5 mL were well-tolerated.

Hematology

No notable mean changes from baseline to follow-up hematology results were observed in TOBI or TPI treatment groups. There were no important differences between TOBI and TPI groups in mean change from baseline and no patterns of increasing mean change with increasing dose of TPI for any hematology test.

No notable increases from baseline to follow-up were observed for TOBI or TPI groups in the frequencies of above-normal or below-normal hematology results. There were no important differences between TOBI and TPI groups and no patterns of increasing frequencies of outlier hematology results with increasing dose of TPI.

One TOBI subject had a clinically significant follow-up eosinophil count that was recorded as an AE.

Serum Chemistry

No notable mean changes from baseline to follow-up serum chemistry results were observed in TOBI or TPI treatment groups. There were no important differences between TOBI and TPI groups in mean change from baseline and no patterns of increasing mean change with increasing dose of TPI for any chemistry test.

No notable increases from baseline to follow-up were observed for TOBI or TPI groups in the frequencies of above-normal or below-normal serum chemistry results. There were no important differences between TOBI and TPI groups and no patterns of increasing frequencies of outlier chemistry results with increasing dose of TPI.

One subject had a clinically significant follow-up glucose result; this result was attributed to CF-related diabetes, was not recorded as an AE, and was not attributed to TPI treatment.

Dipstick Urine Protein

Quantitative changes from baseline to follow-up results were not calculated since the dipstick urine protein test is a qualitative test. No notable increases from baseline to follow-up were observed for TOBI or TPI groups in the frequency of dipstick urine protein results of positive 2+ or greater.

A single positive 3+ result was noted in a subject who received TPI 4×28 mg dose.

Individual Hematology Abnormalities

With one exception, no clinically significant hematology results were observed during the study. TOBI subject 12/405 had a clinically significant follow-up eosinophil result of 9.0% (normal range, 0 to 6%) that was recorded as an AE and was considered possibly related to TOBI treatment by the investigator. The subject's baseline eosinophil result was at the upper limit of normal (5.9%), but the subject had elevated eosinophils 8 days before the baseline result. The clinical importance of the final eosinophil result of 9.0% is uncertain.

Serum Chemistry

With one exception, no clinically significant serum chemistry results were observed during the study. One subject (TPI 3×28 mg) had a clinically significant follow-up glucose result; this result was attributed to CF-related diabetes.

Dipstick Urine Protein

With one exception, no clinically significant dipstick urine protein results were observed during the study. One subject (TPI 4×28 mg) had a positive 3+ result at day 6 follow-up; the subject had a positive 1+ result at screening and at an unscheduled repeat test on the day of dosing. The study coordinator felt that the 3+ urine protein result was consistent with SAEs (cough and sputum increased) beginning on day 2 that led to hospitalization of the subject.

Bronchospasm and Acute Decrease in Pulmonary Function

A single instance of asymptomatic bronchospasm (20.9% reduction in $FEV_1$ percent predicted within 30 minutes after the subject inhaled a single dose of TPI 2×28 mg; (Table 11) was observed during a spirometry procedure that was not performed according to American Thoracic Society (ATS) specifications. Had the procedure been performed to specification, the $FEV_1$ reduction could have been less (11%). A similar asymptomatic reduction in $FEV_1$ percent predicted was also observed in a TOBI subject (19.1% decrease).

One other TOBI subject and six other TPI subjects experienced a decrease of more than 10% but less than 20% in $FEV_1$ percent predicted (Table 11). Three of the six TPI subjects (subject 02/507 at the TPI 3×28 mg dose and subjects 01/415 and 08/406 at the TPI 4×28 mg dose) experienced cough or cough aggravated within minutes after dosing.

TABLE 11

Subjects with Acute Decreases in Pulmonary Function

| Treatment | Predose FEV$_1$ % Predicted | 30-minute Postdose FEV$_1$ % Predicted | Percent Change in FEV$_1$ % Predicted | Associated AEs (especially cough, wheeze, or dyspnea) before/during spirometry? |
|---|---|---|---|---|
| TPI 4 × 14 mg | 52.3 | 44.3 | −15.3 [a] | No |
| TPI 2 × 28 mg | 69.9 | 55.3 | −20.9 [b] | No |
| TPI 3 × 28 mg | 54.3 | 47.6 | −12.3 [a] | No |
|  | 87.4 | 77.1 | −11.8 [a] | Cough at time of spirometry |
| TPI 4 × 28 mg | 73.3 | 64.0 | −12.7 [a] | Cough aggravated, lacrimation increased at time of spirometry |
|  | 77.2 | 67.8 | −12.1 [a] | No |
|  | 67.8 | 60.0 | −11.4 [a] | Cough aggravated, dizziness ending about 30 minutes before spirometry |
| TOBI 300 mg | 39.3 | 34.1 | −13.2 [a] | No |
|  | 104.3 | 84.3 | −19.1 [a] | No |

[a] Decrease in FEV$_1$ % predicted is 10% or more but less man 20%.
[b] Decrease in FEV$_1$ % predicted is 20% or more.

Quantitative Changes in Pulmonary Function

Mean changes in FEV$_1$ percent predicted, FVC percent predicted, and FEF$_{25-75}$ percent predicted in TOBI and all TPI groups were relatively stable from screening to before day 1 dosing and from predose day 1 to day 8 follow-up. There were no apparent differences between TOBI and TPI groups, and no apparent dose-related differences between TPI groups, in mean changes in FEV$_1$, FVC, or FEF$_{25-75}$ percent predicted from before to 30 minutes after dosing.

Vital Signs

There were no large or consistent differences between TPI and TOBI groups in vital signs or changes in vital signs throughout the study.

Concomitant Medications

Thirty-eight of 90 subjects took concomitant medications and therapies after dosing. No differences were apparent in the frequencies or types of concomitant medications and therapies.

Safety Conclusions

More TPI subjects (60.6%) than TOBI subjects (30.0%) experienced treatment-emergent AEs during or after treatment. The percent of subjects with any AE was similar among the TPI dose levels (45% to 69%); sample sizes were too small to determine whether a trend was present for increasing any-AE incidence with increasing TPI dose. All treatment-emergent AEs were mild or moderate in intensity.

One TPI 4×28 mg subject experienced two SAEs (moderate cough and sputum increased indicative of an exacerbation of CF lung disease) that led to hospitalization on the eighth day after the single-dose study treatment was administered; neither of these SAEs was considered related to TPI treatment. Another TPI 4×28 mg subject experienced moderate, probably-related cough aggravated, dysgeusia, and lacrimation increased that caused study drug administration to be interrupted and then stopped; the subject then withdrew consent and was withdrawn from the study. Four subjects experienced coughing during inhalation of TPI that led to a modification, interruption, or delay in dosing (one subject each at TPI 4×14 mg and 4×28 mg and two subjects at 3×28 mg); each AE was considered to be probably related to TPI treatment by the investigator. However, in all four cases, dosing was only interrupted briefly, and the subjects resumed and completed dosing without mishap. All subjects in this study reported respiratory baseline symptoms, with ~90% in each cohort reporting cough. Furthermore the reporting of mild cough is not unexpected from the first administration of a dry powder inhaler, especially when airway irritability is already present.

AEs experienced by the largest number of TPI subjects were cough or cough aggravated (13 of 66 subjects=19.7%); dysgeusia (11 subjects, 16.7%); pharyngitis, haemoptysis, and rhinorrhea (4 subjects, 6.1% each); sputum increased, crackles lung, lacrimation increased, abdominal pain upper, dizziness, headache NOS, and throat irritation (3 subjects, 4.5% each). The incidence of cough, cough aggravated, and dysgeusia increased slightly with increasing TPI dose. No more than one TOBI subject experienced any AE. TOBI subjects experienced no cough, cough aggravated, or dysgeusia, but 85% of the TOBI recipients were chronic TOBI users.

The investigators considered most instances of cough and cough aggravated, all instances of dysgeusia, and most instances of haemoptysis and throat irritation to be possibly or probably related to TPI treatment. By comparison, single instances of chest tightness, herpes simplex, eosinophil count increased, dry throat, pharyngitis, sputum increased, and sputum viscosity increased were considered related to TOBI treatment.

A single instance of asymptomatic bronchospasm (20.9% reduction in FEV$_1$) was recorded, similar to an asymptomatic 19.1% reduction in a TOM subject.

There were no notable changes from baseline in clinical laboratory results, no patterns of increasing change with increasing dose of TPI, no increases in the frequency of above-normal or below-normal results, and no apparent TPI vs. TOBI differences. In a single TOBI subject, an elevated eosinophil count was recorded as an AE.

DISCUSSION AND OVERALL CONCLUSIONS

Single dose administration of TPI results in a more efficient delivery of tobramycin than TOBI® Tobramycin Solution for Inhalation, while maintaining similar tobramycin pharmacokinetics. Systemic exposures achieved after administration of TOBI® Tobramycin Solution for Inhalation were very similar to that seen after administration of 4×28 mg capsules of TPI, with an equivalent dose calculation of 115 mg of TPI. Hence, four capsules of 28 mg TPI (112 mg total) should produce systemic exposures that are comparable to 300 mg of TOBI® Tobramycin Solution for Inhalation.

Minimal dosing interruptions (temporary in all but one case) due to cough were observed and did not appear to alter the single dose pharmacokinetics of tobramycin in serum after administration of TPI.

Approximately 20% of subjects reported cough with TPI, in most cases mild, occasionally causing brief dose interruption, and generally settling quickly. Cough is an expected AE with all inhaled dry powder therapy and was present in the majority of subjects at baseline. While the incidence of AEs was higher in TPI-treated than TOBI-treated subjects, the majority of subjects in most cohorts received chronic cycling TOBI® Tobramycin Solution for Inhalation.

In one case, a young subject forgot to take his usual medication (consisting of a long-acting bronchodilator) and experienced moderate cough after dosing, which led to his withdrawal. The loss of usual bronchoprotection is likely the cause of this reaction.

Administration of single doses of TPI in total doses of 28 mg to 112 mg was well-tolerated by CF subjects during the study. One hundred twelve milligrams of TPI powder gives a close systemic exposure to tobramycin to that from TOBI® Tobramycin Solution for Inhalation.

This study demonstrated that the inhalation using the methods of the invention with a simple inhaler device is much more rapid and efficient than the standard dose of TOBI® Tobramycin Solution for Inhalation by nebulization. The side effects of increased cough and throat irritation after inhalation of TPI were not unexpected, given the amount of powder contained in each dose. However, in most cases the effects were mild, and the subjects voiced an appreciation for how quick and simple the dosing was for TPI. The lack of complaint of cough and bad taste from the TOBI® Tobramycin Solution for Inhalation group may be related to the fact that 85% of those subjects had been taking TOBI® Tobramycin Solution for Inhalation on a routine basis prior to the study. These subjects may have acclimated to the effects of the wet aerosol form of tobramycin.

Thus, single dose administration of dry powder tobramycin resulted in a more efficient delivery of tobramycin than TOBI® Tobramycin Solution for Inhalation, while maintaining similar tobramycin pharmacokinetics. Systemic exposures achieved after administration of TOBI® Tobramycin Solution for Inhalation were very similar to that seen after administration of 4×28 mg capsules of TIP, with an equivalent dose calculation of 115 mg of TIP. Hence, four capsules of 28 mg TIP (112 mg total) should produce systemic exposures that are comparable to 300 mg of TOBI® Tobramycin Solution for Inhalation.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of reducing the amount of time to administer a therapeutic amount of tobramycin to treat a *Pseudomonas aeruginosa* endobronchial infection in a cystic fibrosis patient, the method comprising formulating for administration via inhalation, in four equal unit doses, phospholipid-based dry powder particles prepared by an emulsification and spray-drying process and comprising 30% to 70% tobramycin wherein the formulation comprising is administered to the endobronchial system of the patient twice a day, whereby the administration delivers a dosage of 110 to approximately 120 mg free base tobramycin.

2. The method of claim 1 wherein the particles comprise tobramycin sulfate.

3. The method of claim 2, wherein the particles are phospholipid-based spherical particles with porous structures.

4. The method of claim 3 wherein the phospholipid comprises disteroyl phosphatidlycholine.

5. The method of claim 3 wherein the particles further comprise calcium chloride.

6. The method of claim 1 wherein the dosage is 110 to approximately 115 mg.

7. The method of claim 1 wherein the dry powder particles are administered for a first treatment period of 20 to 36 days.

8. The method of claim 7 wherein the first treatment period is 28 days.

9. The method of claim 7 wherein the first treatment period is followed by a second period of 26 to 30 days during which no aminoglycoside antibiotic is administered to the endobronchial system of the patient.

10. The method of claim 9 wherein the first treatment period and the second non-treatment period are repeated at least one time.

11. The method of claim 1 wherein the dry powder particles are administered using a dry powder inhaler.

12. The method of claim 11 wherein the inhaler is a T-326 inhaler.

13. A method of treating a *Pseudomonas aeruginosa* endobronchial infection in a cystic fibrosis patient, comprising administering via inhalation in four equal 28 mg unit doses of dry powder particles prepared by an emulsification and spray-drying process and comprising approximately 30% to 70% tobramycin wherein the particles are administered to the endobronchial system of the patient twice a day, in which the dry powder particles comprise phospholipid-based spherical particles with porous structures, the particles comprising disteroyl phosphatidlycholine and calcium chloride, whereby the administration delivers a dosage of 110 to approximately 120 mg free base tobramycin.

14. The method of claim 6 wherein the dosage is 112 mg.

15. The method of claim 13 wherein the dosage is 112 mg.

16. The method of claim 13 wherein a serum concentration of tobramycin is substantially similar to a serum concentration of nebulized liquid tobramycin.

17. The method of claim 13 wherein a mean serum concentration-time profile of tobramycin is substantially similar to a mean concentration-time profile of nebulized liquid tobramycin.

* * * * *